(12) United States Patent
Gill et al.

(10) Patent No.: US 6,787,642 B2
(45) Date of Patent: Sep. 7, 2004

(54) USE OF INSECT CELL MEMBRANE TRANSPORTERS AS NOVEL TARGET SITES FOR INSPECTION

(75) Inventors: Sarjeet Gill, Riverside, CA (US); Linda S. Ross, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 72 days.

(21) Appl. No.: 09/815,923

(22) Filed: Mar. 23, 2001

(65) Prior Publication Data

US 2002/0197644 A1 Dec. 26, 2002

(51) Int. Cl.$^7$ .............................................. C07H 21/04
(52) U.S. Cl. ...................... 536/23.1; 530/350; 530/858; 435/325; 435/361
(58) Field of Search ....................... 435/7.1, 325, 361; 536/23.1; 530/325, 361

(56) References Cited

U.S. PATENT DOCUMENTS 5,366,975 A 11/1994 Nathanson et al.

OTHER PUBLICATIONS

Attwood, T. K.; Miller, C. J. "Which craft is best in bioinformatics" Computers and Chemistry 2001, 25, 329–339.*

Ponting, C. P. "Issues in predicting protein function from sequence" Brief. Bioinform. Mar. 2001, vol. 2(1), pp. 19–29.*

Voet, D. and Voet, J. G. Biochemistry. New York: John Wiley and Sons 1995, pp. 126–128, section 6–3A and p. 230, col. 2, first paragraph.*

Demchyshyn, L. L.; Pristupa, Z. B.; Sugamori, K. S.; Barker, E. L.; Blakely, R. D.; Wolfgang, W. J.; Forte, M. A.; Niznik, H. B. Proc. Ntal. Acad. Sci. USA May 1994, 91, 5158–5162.*

Kitamoto, Toshihiro, et al.; "Structure and Organization of the Drosophila Cholinergic Locus"; *The Journal of Biological Chemistry*, Jan. 30, 1998; pp 2706–2713; vol. 273, No. 5; USA.

Burmester, T. and K. Scheller; "Ligands and Receptors: Common Theme in Insect Storage Protein Transport"; *Naturwissenschaften*; 1999; pp. 468–474; vol. 86, No. 10; Springer–Vertag.

* cited by examiner

Primary Examiner—Bennett Celsa
Assistant Examiner—Jon D. Epperson
(74) Attorney, Agent, or Firm—Townsend & Townsend & Crew LLP

(57) ABSTRACT

The present invention discloses the existence of novel insect transporters that can be used as targets for screening of new insecticides. This invention provides nucleic acids which encode the following insect cell membrane transporters: acetylcholine transporters, serotonin transporters, proline transporters, glutamate transporters, neurotransmitter transporters encoded by the inebriated gene, orphan transporters, GABA transporters, and LAT transporters. The invention also provides the polypeptides, cells expressing the polypeptides, and methods of using the nucleic acids and polypeptides to identify compounds which bind to or modulate the activity of the above-listed insect cell membrane transporters.

8 Claims, No Drawings

SEQUENCE LISTING

<160> NUMBER OF SEQ ID NOS: 20

<210> SEQ ID NO 1
<211> LENGTH: 5554
<212> TYPE: DNA
<213> ORGANISM: Manduca sexta
<220> FEATURE:
<223> OTHER INFORMATION: vesicular acetylcholine transporter

<400> SEQUENCE: 1

```
gagactcagg ttccgaagtc ctatccgagg gtcgacgagt cctgttcgtg gacgccgcgt        60
aaatgtactg actactgtga gcgacgcgag tgtaccatcc gcaacgtaac cagctctaga       120
agatgaacac agatccccag cagttagaat attaacgtga tacacaagta gttaacatgg       180
cggagggacc acagacaata tggcagaaga tcgacaactc catcatcccc gtcataaacc       240
tggaggtgcg ggaggtccgg gagatattat gggagaagat acaggaaccc acctcacaga       300
ggaagatcat cctggtgata gtgtccatag cgctgctatt agacaacatg ttgtatatgg       360
tgatcgtgcc tatcatcccg gactacttga ggtatatagg cgcatgggga gaggcaggct       420
acgaccatgt cgttaccttg ccgcccatca gagagggtaa caggaccatc ataccgacca       480
agattatacc cgcgtcacac catggtcagg actctgcgac gggagtgctc ttcgcgtcca       540
aagctatagt gcagctcatg ataaaccctt tctccggtgc cttaattgac cgcataggt       600 acgatatacc catgatgata ggactcataa taatgttcct atcgacctca atattcgcgt       660
gcggtcggag ttacagcatg ttgttcttcg cgaggagtct ccagggagta ggatcggcgt       720
ttgctgatac ttcagggctg gccatgattg ctgaccggtt tactgaagaa agtgagcgct       780
caaaggctct tggaattgcc ctcgcattta taagtttcgg aagccttgta gcgccaccttt       840
```

```
ttggaggtgc tttgtatcag tttgcgggta aagaagtacc gtttcttatt ctcgctctga    900
tatctttaat ggatggattc atgctgctat tggtaatgaa accaattaaa acgcagatga    960
aagaagcgaa ccaaccgaag ccagctggca ctccgatatg gaaactcctc atggacccgt   1020
atatcgcagt atgtgctgga gctctcatga tgtctaacgc tgctttggct ttcctcgagc   1080
ctacaatttc ctcctggatg gaagataact tgaccaaaga caattggaag attggcatga   1140
tatggctacc agctttcttc ccgcacgttc ttggggtaat catcacagta aagatggcaa   1200
agaaataccc acaacaacaa tggctgatgg ctgctggtgg attggcttta gaaggattgt   1260
gctgtttcat tattccgttc gcgagttcgt acaaaatgct catgatacct atttgcggca   1320
tctgtttcgg gatcgcgttg attgacactg ctctactgcc caccctgggt tacctggtcg   1380
atgttcggta cgtttctgtg tacgaagca tctacgcaat cgctgatata tcatattcat   1440
tcgcgtatgc tgtggggccg attatagcag gagaagtggt cgaagccatt ggcttcactg   1500
ctctgaatct cctaattgct ttcagcaacc tcctgtatgc cccagtactt atgtacctca   1560
ggcacatcta cgactttaaa ccatttgaga acgaagcaaa tattctcatg tctgacccgc   1620
cggataaaga ataccaaacg tacagcatgc aagatcagag gcccgtcaac ggtgaataca   1680
aaaccatttt ggaatattcc aacgtgtctg acaagtggc agcaacgcag gagtcgaatg   1740
tggacgccgc gcagactggc tactcatacg accagtcgta tcaggggat atcagaact   1800
acagccaggc tacgagcagg agtaccagca ccaaccggag tacaaccagc cgcggcagtt   1860
gcctgcccag ccgcagcccg cgcctagcaa tccgttccgc gcaggcacgg cagcggctcc   1920
cgcacccgcg cccgcgccag ccccgcctgc tcccaccatc aagaacccgt tccggcaagg   1980
cttctaaatt ttattcagtg ttgttgtcga tattttgaa tttacttgtt gtttaattat   2040
aaagttctca ggtaatgcct tcgatcactg agccgcgtca catcggcggc gggtttagtc   2100
tctgttaggt gtctattaga tgtgcttaaa ctgtagttgt gcgagtgatg tacgtagact   2160
caccaggtaa tgtgaacctg ccgggcccta tgtacaccac tccagctgtt ttcttgttga   2220
tcttgtactg ttctaaaact gttatgtctt ctgatatata agtataacaa tgtgtaagta   2280
ataataagaa atatagcggc gtaaatctcg atgtacactc gaaatagaca tgaaattctt   2340
aaagatatat cgtttggggt gtatatagat acattgtata aacgtatata ctggcacacg   2400
attcacgttg cactaggtaa gggcctaaga aatatttatt ggtgaaatct tggcacttac   2460
gggcatttta atgatctcgc ttttgtgtaa cttgatgtga agctacatag gtgcgtggga   2520
catagattgt gggtggaatt tattataatt atattagatg acgtcaagcg ttggacgtgc   2580
gacagcgacg caggccttgg tgacgtaatc aagtcttcat aaactgcgaa atatcataca   2640
attgctgtgt cactatcgct acgtcattga ctcgacgtta ggactacaaa tggtagtaca   2700
tactacgata taactgatta actatttaaa tgaaagtatc aacatacaaa ttctgactac   2760
aatctatact aagctcagaa ttgtaattat gtatgtgtca ttatatttt agacgtacta   2820
taagatattt cctatgctat atcagcaata ttagtgtacg gcttcataat tattctatat   2880
caatagttgt aggttagtat caacttgtga taagttgcaa ccaagtaacg aaacatatca   2940
ggatctttg atccacgtaa cttaagttag agtaatgagg taagtgtata agtggtagta   3000
aggccacgtt ttagcttaaa atcaggtaca tcgatttaac gtttggtggg atgatatcgt   3060
atttcttgtt tagagtccga aattaacatt atagctactt gcaaaaagta tgactgaaga   3120
atggaaggtt caatatatac taatacatat caaataaaga agaaatgtta tgaaaatgtg   3180
agggaaagaa actataacga tattggaaat ttcgtatgtt aatataactt atataacaga   3240
```

-continued

```
atttgtttgt tataaaatct aatgaaagag taaatagtat tagagaatgt ttcaatgata    3300
ttagaattct acaaaaacct actactaatc aactttatat acctccatta ggtaagtaaa    3360
gatctcatcc caccgaaccg tttacaaaac ggaagattca attcaattgt aaagtaattg    3420
tagaagatat cgcgacgagc ccgacatgtc aattgaacga atgtataaag taaaacttta    3480
cgtgtaatat atggatattt aaaattatta tgtacacatt cgtttgaacc acgctggcac    3540
cgcgcggtcg ccaaccgctt tagttcagtg tgatgggtgt cctttcatta gactagagac    3600
aggcaggagg cattgtatct ggtggagacc gtcatgcctg gcgatcagct gtccaagact    3660
gcaccaagtg acagggtca cgatcctcag cattgaggga aagattagag agagagagag    3720
agagagagat acgccattcc aacatgtaaa gcataacagg tctgtacaag gagagaccca    3780
taatgtttac catgacacat actttgtgtg atacgctaaa tacttctagt cagagtgtag    3840
cggaaagctc aaagttgatg ctcatgacaa agggtactt ggtgtaacca acattaagta    3900
atgaattggt aatactaact tcaaggatat aagacatgaa tcacgtaatg aataacgatt    3960
caacacttta gaaccgatat ggatttttct atttatccac tcctgcgaca aggcgtttga    4020
caactggtca tactatattt ttcgttgtcg cactgttagc aagaacatgc acaagatatt    4080
tcagacctgg tttcgcacta aacgtgattg aaacgagaaa tctatttgga tgtttatgaa    4140
aggatattca tcacaaattc ctaaggtcat aaaatttgtg tttggttaag aagaaattta    4200
tacctagcct gcaaagtaca atagcatttg tagttcagac tgtctgcaca tcgtattgtt    4260
tcgcgcactg cacttctaca ttatgattaa tgcgctgatg atcgtcattg agcaattaaa    4320
aaaaaatgaa gtaagaaggg gtccttatta tatatatctc agagcatctt gtctttttc    4380 tttcaggatg gcagaagtat tataatctta ttccttttt ttatatcgga aatttattgt    4440
agtgtaaata ttgaagaatt atgatatttt ctccatttat tttctataag gaaatattgt    4500
attataatga tattcctaaa atatttgcat tcattttaa ataatatata ttaatatcaa    4560
aatcgtgcac acaactaaat gacgaatcta taaacctttt aaacctctga acaatatta    4620 atgttgaacg ataaatatac aataaaccac gagagcttaa ataagctctg ttataaagcc    4680
accgcactca ctttattgtt tgttgtttaa tatttacctt tccattaaag tcaaagtgta    4740
ctttatattt aatgtgatat atatttttt tatattgctt gattgaggta gtcagcgcat    4800
taagaacctt atttctctag tgggttccct acgatagccg tgctgtaatg taacaattga    4860
cgttaaacgc cgttgtataa cgaccgttat ataacgacgt cgctatccta gcaacctatg    4920
cttagatact tttgtatatt ttaatatgta acctaatttt cgcatatttc tatattaagg    4980
tattttcaac atataataat gtatattgtg taacggactc tccgtgtata taaggataga    5040
gtcaattttc ttgtcaaatt ctcccgaaat tcaattaatt agtagtgtgt gaagtgtaca    5100
agtatgatta aggatgtata ttgctgtgta tattgataag ctaaggtata tgttgctctg    5160
ttctatagcc ttaccttcac catctattcc ggttctatat tcggttaaat acttcgatta    5220
taaatatctg ttaccgccta gtgttatgtc gtaaatctgg tgatttaatt tttggtattt    5280
gtatctaata ttgcgtcatt ttgctagtgg agttttgctt cctctcttct ctatgttaag    5340
gtgtatattt ctttaacaat caacatacac gagcgatgtt caggaagtat gttgtgattg    5400
ggtaacatat tctattagta tgtgcaatta tagtgacgta cttattactg tatattgtga    5460
ttctgttgtg aggggaatta aaattgcatt tggtaaaaaa aaaaaaaaaa aaaaaaaaa    5520 aaaaaaaaaa aaaaaaaaaa aaaaaaaaaa aaaa                                 5554
```

```
<210> SEQ ID NO 2
<211> LENGTH: 619
<212> TYPE: PRT
<213> ORGANISM: Manduca sexta
<220> FEATURE:
<223> OTHER INFORMATION: vesicular acetylcholine transporter

<400> SEQUENCE: 2
```

| | | | | | | | | | | | | | | |
|---|---|---|---|---|---|---|---|---|---|---|---|---|---|---|
| Met | Ala | Glu | Gly | Pro | Gln | Thr | Ile | Trp | Gln | Lys | Ile | Asp | Asn | Ser | Ile |
| 1 | | | | 5 | | | | | 10 | | | | | 15 | |

Ile Pro Val Ile Asn Leu Glu Val Arg Glu Val Arg Glu Ile Leu Trp
                20                  25                  30

Glu Lys Ile Gln Glu Pro Thr Ser Gln Arg Lys Ile Ile Leu Val Ile
            35                  40                  45

Val Ser Ile Ala Leu Leu Asp Asn Met Leu Tyr Met Val Ile Val
    50                  55                  60

Pro Ile Ile Pro Asp Tyr Leu Arg Tyr Ile Gly Ala Trp Gly Glu Ala
65                  70                  75                  80

Gly Tyr Asp His Val Val Thr Leu Pro Pro Ile Arg Glu Gly Asn Arg
                85                  90                  95

Thr Ile Ile Pro Thr Lys Ile Ile Pro Ala Ser His His Gly Gln Asp
            100                 105                 110

Ser Ala Thr Gly Val Leu Phe Ala Ser Lys Ala Ile Val Gln Leu Met
            115                 120                 125

Ile Asn Pro Phe Ser Gly Ala Leu Ile Asp Arg Ile Gly Tyr Asp Ile
        130                 135                 140

Pro Met Met Ile Gly Leu Ile Ile Met Phe Leu Ser Thr Ser Ile Phe
145                 150                 155                 160

Ala Cys Gly Arg Ser Tyr Ser Met Leu Phe Phe Ala Arg Ser Leu Gln
                165                 170                 175

Gly Ile Gly Ser Ala Phe Ala Asp Thr Ser Gly Leu Ala Met Ile Ala
            180                 185                 190

Asp Arg Phe Thr Glu Glu Ser Glu Arg Ser Lys Ala Leu Gly Ile Ala
        195                 200                 205

Leu Ala Phe Ile Ser Phe Gly Ser Leu Val Ala Pro Pro Phe Gly Gly
210                 215                 220

Ala Leu Tyr Gln Phe Ala Gly Lys Glu Val Pro Phe Leu Ile Leu Ala
225                 230                 235                 240

Leu Ile Ser Leu Met Asp Gly Phe Met Leu Leu Val Met Lys Pro
                245                 250                 255

Ile Lys Thr Gln Met Lys Glu Ala Asn Gln Pro Lys Pro Ala Gly Thr
            260                 265                 270

Pro Ile Trp Lys Leu Leu Met Asp Pro Tyr Ile Ala Val Cys Ala Gly
        275                 280                 285

Ala Leu Met Met Ser Asn Ala Ala Leu Ala Phe Leu Glu Pro Thr Ile
            290                 295                 300

Ser Ser Trp Met Glu Asp Asn Leu Thr Lys Asp Asn Trp Lys Ile Gly
305                 310                 315                 320

Met Ile Trp Leu Pro Ala Phe Phe Pro His Val Leu Gly Val Ile Ile
                325                 330                 335

Thr Val Lys Met Ala Lys Lys Tyr Pro Gln Gln Gln Trp Leu Met Ala
            340                 345                 350

Ala Gly Gly Leu Ala Leu Glu Gly Leu Cys Cys Phe Ile Ile Pro Phe
            355                 360                 365

```
Ala Ser Ser Tyr Lys Met Leu Met Ile Pro Ile Cys Gly Ile Cys Phe
    370                 375                 380

Gly Ile Ala Leu Ile Asp Thr Ala Leu Leu Pro Thr Leu Gly Tyr Leu
385                 390                 395                 400

Val Asp Val Arg Tyr Val Ser Val Tyr Gly Ser Ile Tyr Ala Ile Ala
                405                 410                 415

Asp Ile Ser Tyr Ser Phe Ala Tyr Ala Val Gly Pro Ile Ile Ala Gly
            420                 425                 430

Glu Val Val Glu Ala Ile Gly Phe Thr Ala Leu Asn Leu Leu Ile Ala
        435                 440                 445

Phe Ser Asn Leu Leu Tyr Ala Pro Val Leu Met Tyr Leu Arg His Ile
    450                 455                 460

Tyr Asp Phe Lys Pro Phe Glu Asn Glu Ala Asn Ile Leu Met Ser Asp
465                 470                 475                 480

Pro Pro Asp Lys Glu Tyr Gln Thr Tyr Ser Met Gln Asp Gln Arg Pro
                485                 490                 495

Val Asn Gly Glu Tyr Lys Asn His Leu Glu Tyr Ser Asn Val Ser Gly
            500                 505                 510

Gln Val Ala Ala Thr Gln Glu Ser Asn Val Asp Ala Ala Gln Thr Gly
        515                 520                 525

Tyr Ser Tyr Asp Gln Ser Tyr Gln Gly Asp Tyr Gln Asn Tyr Ser Gln
    530                 535                 540

Ala Thr Ser Arg Ser Thr Ser Thr Asn Arg Ser Thr Thr Ser Arg Gly
545                 550                 555                 560

Ser Cys Leu Pro Ser Arg Ser Pro Arg Leu Ala Ile Arg Ser Ala Gln
                565                 570                 575

Ala Arg Gln Arg Leu Pro His Pro Arg Pro Gln Pro Arg Leu Leu
            580                 585                 590

Pro Pro Ser Arg Thr Arg Ser Gly Lys Ala Ser Lys Phe Tyr Ser Val
    595                 600                 605

Leu Leu Ser Ile Phe Leu Asn Leu Leu Val Val
    610                 615

<210> SEQ ID NO 3
<211> LENGTH: 1764
<212> TYPE: DNA
<213> ORGANISM: Manduca sexta
<220> FEATURE:
<223> OTHER INFORMATION: serotonin transporter

<400> SEQUENCE: 3
atgccgccgt cggacgcgcc gcccgcgccc accgcgccac ctcctgatct tcctgctacc      60
accgctcaga aaagccgttc ggtggtggtg tcgcttacgc cggcgcggca gcgcgagacc     120
tgggcgaaga aggcagagtt cctgctggcg gtggtgggat cgcagtgga tcttggtaac     180 gtgtggcgat tccctacat ctgttaccag aatggaggcg gtgcgttcct gatcccgtac     240
tgcgttatgc tgctgttttgg cgggctgccg ctgttcttcc tggaactggc gctgggccag     300
taccaccgct gcggctgcct cactctctgg aaacggatct gccccgcgct taaaggtgtc     360
ggctatgcca tctgcatgat cgacatctac atgggcatgt actacaacac gatcatcgga     420
tgggcggtgt attacctgat cgcttctctc gcgtctataa actctgtgct gccatggacc     480
agctgcgaca acgagtggaa cacgccgctg tgcacgccgg tcacctcacc tcagactaat     540
cctaactctt ctacaccggc gaaggagttc ttcgaacgta atgtattgga gcagcacaag     600
tctaacggcc tggatgacat ggggccgatc aagccgtcgc tggctctgtg tgtgttcggg     660
```

-continued

```
gtctttgtcc tcgtctactt ctccttgtgg aaaggagtca ggagtgctgg caaggtggtg      720
tgggtgacag ctctggcccc gtacgtggtg ctgctgattc tgctggcgag aggcgtcacg      780
cttccaggag cgacggaggg catacgctac taccttaccc cagagtggca caaattgcaa      840
aactctaagg tatggattga cgcggcatcc cagattttct tctcgctcgg tcccgggttc      900
ggaaccctac tggcgctctc cagctacaac aagttcaaca caactgcta cagggacgcg       960 ctcatcactt cttctatcaa ctgcttgacc agcttccttg ctggtttcgt cattttctcg     1020
gttttggggt acatggcgca cgttcagaac aagagcatcg aggaggttgg cctcgaaggc     1080
cctggactgg tgttcatcgt gtaccccgag gccatcgcca ccatgaccgg ctccgtgttc     1140
tgggccatca tcttcttcct catgcttatt accctgggac ttgacagtac ttttggaggt     1200
cttgaggcag tcaccacggc tctttgcgac gaatatcctc gagtgttagg cagacatcgc     1260
gaagtatttg tggctgtact gcttctgttc atctatattt gcgctctgcc caccaccaca     1320
tacggtggtg tatacctcgt agacctactc aatgtgtatg gccctggatt ggcgattcta     1380
ttcgtggtat ttgctgaggc tgccggcgtg tgctgggtgt atggcgtcga ccggttctct     1440
gaagatgtga ggaccatgct ggggcacacc cctggatggt tctggaggac ctgttggtct     1500
tacatcagtc ccgtattctt gctggtgctg ttcgtgttct ccgttctggc acacgaggag     1560
atgctcggcg gggaatacac ctatccctca tggtctatca ccgtaggctg ggtgatgacc     1620
ggcaccaccg tctcgtgcat tcctctttac attatctaca aactgctcat cactcctggc     1680
aattgcatca accgcatcaa gacaatccaa cgtccggaag tgacgtcgat acctccagcg     1740
gactctaccc tatgcaacct gtga                                            1764
```

<210> SEQ ID NO 4
<211> LENGTH: 587
<212> TYPE: PRT
<213> ORGANISM: Manduca sexta
<220> FEATURE:
<223> OTHER INFORMATION: serotonin transporter

<400> SEQUENCE: 4

```
Met Pro Pro Ser Asp Ala Pro Pro Ala Pro Thr Ala Pro Pro Asp
  1               5                  10                  15

Leu Pro Ala Thr Thr Ala Gln Lys Ser Arg Ser Val Val Val Ser Leu
                 20                  25                  30

Thr Pro Ala Arg Gln Arg Glu Thr Trp Ala Lys Lys Ala Glu Phe Leu
             35                  40                  45

Leu Ala Val Val Gly Phe Ala Val Asp Leu Gly Asn Val Trp Arg Phe
         50                  55                  60

Pro Tyr Ile Cys Tyr Gln Asn Gly Gly Gly Ala Phe Leu Ile Pro Tyr
 65                  70                  75                  80

Cys Val Met Leu Leu Phe Gly Gly Leu Pro Leu Phe Phe Leu Glu Leu
                 85                  90                  95

Ala Leu Gly Gln Tyr His Arg Cys Gly Cys Leu Thr Leu Trp Lys Arg
            100                 105                 110

Ile Cys Pro Ala Leu Lys Gly Val Gly Tyr Ala Ile Cys Met Ile Asp
        115                 120                 125

Ile Tyr Met Gly Met Tyr Tyr Asn Thr Ile Ile Gly Trp Ala Val Tyr
    130                 135                 140

Tyr Leu Ile Ala Ser Leu Ala Ser Ile Asn Ser Val Leu Pro Trp Thr
145                 150                 155                 160
```

-continued

```
Ser Cys Asp Asn Glu Trp Asn Thr Pro Leu Cys Thr Pro Val Thr Ser
            165                 170                 175

Pro Gln Thr Asn Pro Asn Ser Thr Pro Ala Lys Glu Phe Phe Glu
        180                 185                 190

Arg Asn Val Leu Glu Gln His Lys Ser Asn Gly Leu Asp Asp Met Gly
            195                 200                 205

Pro Ile Lys Pro Ser Leu Ala Leu Cys Val Phe Gly Val Phe Val Leu
        210                 215                 220

Val Tyr Phe Ser Leu Trp Lys Gly Val Arg Ser Ala Gly Lys Val Val
225                 230                 235                 240

Trp Val Thr Ala Leu Ala Pro Tyr Val Leu Leu Ile Leu Leu Ala
                245                 250                 255

Arg Gly Val Thr Leu Pro Gly Ala Thr Glu Gly Ile Arg Tyr Tyr Leu
                260                 265                 270

Thr Pro Glu Trp His Lys Leu Gln Asn Ser Lys Val Trp Ile Asp Ala
            275                 280                 285

Ala Ser Gln Ile Phe Phe Ser Leu Gly Pro Gly Phe Gly Thr Leu Leu
            290                 295                 300

Ala Leu Ser Ser Tyr Asn Lys Phe Asn Asn Asn Cys Tyr Arg Asp Ala
305                 310                 315                 320

Leu Ile Thr Ser Ser Ile Asn Cys Leu Thr Ser Phe Leu Ala Gly Phe
                325                 330                 335

Val Ile Phe Ser Val Leu Gly Tyr Met Ala His Val Gln Asn Lys Ser
                340                 345                 350

Ile Glu Glu Val Gly Leu Glu Gly Pro Gly Leu Val Phe Ile Val Tyr
            355                 360                 365

Pro Glu Ala Ile Ala Thr Met Thr Gly Ser Val Phe Trp Ala Ile Ile
        370                 375                 380

Phe Phe Leu Met Leu Ile Thr Leu Gly Leu Asp Ser Thr Phe Gly Gly
385                 390                 395                 400

Leu Glu Ala Val Thr Thr Ala Leu Cys Asp Glu Tyr Pro Arg Val Leu
                405                 410                 415

Gly Arg His Arg Glu Val Phe Val Ala Val Leu Leu Leu Phe Ile Tyr
            420                 425                 430

Ile Cys Ala Leu Pro Thr Thr Thr Tyr Gly Gly Val Tyr Leu Val Asp
        435                 440                 445

Leu Leu Asn Val Tyr Gly Pro Gly Leu Ala Ile Leu Phe Val Val Phe
450                 455                 460

Ala Glu Ala Ala Gly Val Cys Trp Val Tyr Gly Val Asp Arg Phe Ser
465                 470                 475                 480

Glu Asp Val Arg Thr Met Leu Gly His Thr Pro Gly Trp Phe Trp Arg
                485                 490                 495

Thr Cys Trp Ser Tyr Ile Ser Pro Val Phe Leu Leu Val Leu Phe Val
            500                 505                 510

Phe Ser Val Leu Ala His Glu Glu Met Leu Gly Gly Glu Tyr Thr Tyr
            515                 520                 525

Pro Ser Trp Ser Ile Thr Val Gly Trp Val Met Thr Gly Thr Thr Val
        530                 535                 540

Ser Cys Ile Pro Leu Tyr Ile Ile Tyr Lys Leu Leu Ile Thr Pro Gly
545                 550                 555                 560

Asn Cys Ile Asn Arg Ile Lys Thr Ile Gln Arg Pro Glu Val Thr Ser
                565                 570                 575

Ile Pro Pro Ala Asp Ser Thr Leu Cys Asn Leu
```

<210> SEQ ID NO 5
<211> LENGTH: 1671
<212> TYPE: DNA
<213> ORGANISM: Manduca sexta
<220> FEATURE:
<223> OTHER INFORMATION: proline transporter

<400> SEQUENCE: 5

```
atgtctggtg ctacgcaaga ccgatgggga agtcagctag aatatttgct atcatgtttg      60
ggatacgccg ttggcatcgg gaacctatgg cggtttccct atttgtgtta tcggaatgga     120
ggaggagcgt ttttgattcc gtatttcctt acgttaatca tatgcggcat acctcttgtc     180
tatctggaaa caacgcttgg acaattcgct agcgctggtt gcatatcggt cttcaatatt     240
aaccctttat tcaaaggtgc aggatacgcc gttatagttc taaatgtaat agcttcgata     300
tacttctcgg cgattatgtc atatccaata ctttacatat atcattcgat gagttccacca    360
ttaccttggc aaagttgtgg caattcctgg aacactgtga actgcaccga ataacagga     420
aactcgagtt ttttcacatc aaacggatct atcactacgc cggaagacga atacttccac    480
cgacacctct tgcaagtctc cccgaatatc aaccatatcg aagtatagt tgctccagtg     540
ttctggtgca acctgatttg ttggattctt gtgtatctgt gcatctgtaa cggggtcaag    600
agcgtcggaa agatcgtata cttcaccgta ttgtttcctt atgtggtctt gtccgtttta    660
ttcgtacgag ggataaccct ccctggcgct tggaagggca tcatgtttta tattcttccc    720
gattgggcac agctagctaa accgaaagta tgggcagatg cagcaacaca aatcttttc    780
tctcttggtc cgggctgggg tggtctcgtc agcatgtcca gtttcaacaa atttcactac    840
aacaacttac ggtcatccat gattattcca atagtgaata gtgcaacaag catctgggcg    900
ggttttgttg tattctcagt gctaggattt gctgctgaac gtactaatgt gccagttagc    960
caagtggcga ccgctggtcc tgggttagca tttgttacgt acccggctac ggtgacgatg   1020
atgccagctc ctaatttgtg ggcaatcaca ttctttgtaa tgctgttttt ccttggaata   1080
gatactatgt tcgtcactat cgaagctata atcgctggat tattggatga gtttcctaga   1140
ttcaaatcac gtaaacgaat aatagctttc atcacctgcg tcgttctttt tagttttttct 1200
attatctgca atactgaggg agggctacat gtgattggat tactagactc ccatgtagcc   1260
atactttgtg tgccgctagt atgcgcgttg gagatcatag cagctgtcta cacatacgaa    1320
aacttcagtt tcgacgtact gttcatgacc ggccgacctt tgagacgaat ctggatggta    1380
ttgtggagat atgttattct tttaatatta ttggtgatca cactgtatag tcttctggaa   1440
gtgtcgagtt tagccggctg gttcattact ctcgtttccg ttgtctgcat accgatttac   1500
gcagctaaag tttactacg ggcagaagga agtctgttgg agcgaatacg tgctagctgc    1560
cgtcctagca acgattgggg tccatcggag ccagaaaaaa gaagggaatg ggagttgctt   1620
aaaaaacaga agctgatat ttttccgttg aatgatttag acaagtatta a              1671
```

<210> SEQ ID NO 6
<211> LENGTH: 556
<212> TYPE: PRT
<213> ORGANISM: Manduca sexta
<220> FEATURE:
<223> OTHER INFORMATION: proline transporter

<400> SEQUENCE: 6

Met Ser Gly Ala Thr Gln Asp Arg Trp Gly Ser Gln Leu Glu Tyr Leu

-continued

```
  1               5                 10                15
Leu Ser Cys Leu Gly Tyr Ala Val Gly Ile Gly Asn Leu Trp Arg Phe
             20                25                30
Pro Tyr Leu Cys Tyr Arg Asn Gly Gly Ala Phe Leu Ile Pro Tyr
             35                40                45
Phe Leu Thr Leu Ile Ile Cys Gly Ile Pro Leu Val Tyr Leu Glu Thr
             50                55                60
Thr Leu Gly Gln Phe Ala Ser Ala Gly Cys Ile Ser Val Phe Asn Ile
 65              70                75                            80
Asn Pro Leu Phe Lys Gly Ala Gly Tyr Ala Val Ile Val Leu Asn Val
                 85                90                95
Ile Ala Ser Ile Tyr Phe Ser Ala Ile Met Ser Tyr Pro Ile Leu Tyr
                100               105               110
Ile Tyr His Ser Met Ser Ser Pro Leu Pro Trp Gln Ser Cys Gly Asn
                115               120               125
Ser Trp Asn Thr Val Asn Cys Thr Glu Ile Thr Gly Asn Ser Ser Phe
                130               135               140
Phe Thr Ser Asn Gly Ser Ile Thr Thr Pro Glu Asp Glu Tyr Phe His
145              150               155                            160
Arg His Leu Leu Gln Val Ser Pro Asn Ile Asn His Ile Gly Ser Ile
                165               170               175
Val Ala Pro Val Phe Trp Cys Asn Leu Ile Cys Trp Ile Leu Val Tyr
                180               185               190
Leu Cys Ile Cys Asn Gly Val Lys Ser Val Gly Lys Ile Val Tyr Phe
             195               200               205
Thr Val Leu Phe Pro Tyr Val Val Leu Ser Val Leu Phe Val Arg Gly
             210               215               220
Ile Thr Leu Pro Gly Ala Trp Lys Gly Ile Met Phe Tyr Ile Leu Pro
225              230               235                            240
Asp Trp Ala Gln Leu Ala Lys Pro Lys Val Trp Ala Asp Ala Ala Thr
                245               250               255
Gln Ile Phe Phe Ser Leu Gly Pro Gly Trp Gly Gly Leu Val Ser Met
                260               265               270
Ser Ser Phe Asn Lys Phe His Tyr Asn Asn Leu Arg Ser Ser Met Ile
                275               280               285
Ile Pro Ile Val Asn Ser Ala Thr Ser Ile Trp Ala Gly Phe Val Val
                290               295               300
Phe Ser Val Leu Gly Phe Ala Ala Glu Arg Thr Asn Val Pro Val Ser
305              310               315                            320
Gln Val Ala Thr Ala Gly Pro Gly Leu Ala Phe Val Thr Tyr Pro Ala
                325               330               335
Thr Val Thr Met Met Pro Ala Pro Asn Leu Trp Ala Ile Thr Phe Phe
                340               345               350
Val Met Leu Phe Phe Leu Gly Ile Asp Thr Met Phe Val Thr Ile Glu
                355               360               365
Ala Ile Ile Ala Gly Leu Leu Asp Glu Phe Pro Arg Phe Lys Ser Arg
                370               375               380
Lys Arg Ile Ile Ala Phe Ile Thr Cys Val Val Leu Phe Ser Phe Ser
385              390               395                            400
Ile Ile Cys Asn Thr Glu Gly Gly Leu His Val Ile Gly Leu Leu Asp
                405               410               415
Ser His Val Ala Ile Leu Cys Val Pro Leu Val Cys Ala Leu Glu Ile
                420               425               430
```

| Ile | Ala | Ala | Val | Tyr | Thr | Tyr | Glu | Asn | Phe | Ser | Phe | Asp | Val | Leu | Phe |
|---|---|---|---|---|---|---|---|---|---|---|---|---|---|---|---|
| | | 435 | | | | 440 | | | | 445 | | | | | |

| Met | Thr | Gly | Arg | Pro | Leu | Arg | Arg | Ile | Trp | Met | Val | Leu | Trp | Arg | Tyr |
|---|---|---|---|---|---|---|---|---|---|---|---|---|---|---|---|
| | 450 | | | | | 455 | | | | | 460 | | | | |

| Val | Ile | Leu | Leu | Ile | Leu | Leu | Val | Ile | Thr | Leu | Tyr | Ser | Leu | Leu | Glu |
|---|---|---|---|---|---|---|---|---|---|---|---|---|---|---|---|
| 465 | | | | | 470 | | | | | 475 | | | | | 480 |

| Val | Ser | Ser | Leu | Ala | Gly | Trp | Phe | Ile | Thr | Leu | Val | Ser | Val | Val | Cys |
|---|---|---|---|---|---|---|---|---|---|---|---|---|---|---|---|
| | | | | 485 | | | | | 490 | | | | | 495 | |

| Ile | Pro | Ile | Tyr | Ala | Ala | Lys | Val | Leu | Leu | Arg | Ala | Glu | Gly | Ser | Leu |
|---|---|---|---|---|---|---|---|---|---|---|---|---|---|---|---|
| | | | 500 | | | | | 505 | | | | | 510 | | |

| Leu | Glu | Arg | Ile | Arg | Ala | Ser | Cys | Arg | Pro | Ser | Asn | Asp | Trp | Gly | Pro |
|---|---|---|---|---|---|---|---|---|---|---|---|---|---|---|---|
| | | | 515 | | | | 520 | | | | | 525 | | | |

| Ser | Glu | Pro | Glu | Lys | Arg | Arg | Glu | Trp | Glu | Leu | Leu | Lys | Lys | Gln | Lys |
|---|---|---|---|---|---|---|---|---|---|---|---|---|---|---|---|
| | 530 | | | | | 535 | | | | | 540 | | | | |

| Ala | Asp | Ile | Phe | Pro | Leu | Asn | Asp | Leu | Asp | Lys | Tyr |
|---|---|---|---|---|---|---|---|---|---|---|---|
| 545 | | | | | 550 | | | | 555 | | |

<210> SEQ ID NO 7
<211> LENGTH: 1995
<212> TYPE: DNA
<213> ORGANISM: Aedes aegypti
<220> FEATURE:
<223> OTHER INFORMATION: glutamate transporter

<400> SEQUENCE: 7

| tttcaaacgt | ggttgaaact | gttgcactaa | tcgctcttca | aatgctgcta | caatagcaat | 60 |
| gatcgtgaaa | cagtttcaaa | cgtggttgaa | tcgtttttttt | tttttttcgtt | ttgagaattt | 120 |
| aaatcttgtc | gagatagaaa | tctttgttca | tgatgaattt | acagtagcac | agagttttaa | 180 |
| acagcaaaat | gtattagaga | tatttgatga | atcacaaaaa | taaccgttcg | tggtattaaa | 240 |
| tagtaatgcg | taatttgatg | agagacccaa | aacgacacag | cgcatttcga | cggcttatcc | 300 |
| gtgcttctga | gcccattagc | agcacgctga | taagatgagg | cgggagcagt | tgcaagcctt | 360 |
| cgtcaaggag | aacctgctga | cgttttttgac | tatcggtgga | gtcatcgttg | catagtgct | 420 |
| tggaattggt | ctcagggaag | tgcccgcgga | aggtgaaaaa | tggacggcaa | gagatgtagc | 480 |
| ctacatcaac | tttgtaggag | atatcttcct | ccggatgctg | aaagcactga | tcctgcctct | 540 |
| gattgttaca | tcgctcatcg | ctgctgtcgg | ttcccttgat | ctgtcgcttt | cgggaaaaat | 600 |
| cggaggtcga | gctgtcctgt | actacgtgat | aacaacggta | atggcagtta | ttttgggaat | 660 |
| tgtactcgtc | gtaaccattc | aaccgggcaa | aggagccgaa | gagacaagtg | gcgctgtaaa | 720 |
| agggaagta | cgaaacgtta | caacggctga | cactttgctg | gacttggtac | gaaacatgtt | 780 |
| tccaccgaac | ctggtccaag | cttgcctaca | gcaatatcaa | actgttctga | cacctcccaa | 840 |
| aagtaacccg | gtggaaacag | atctgatcct | tggtctgtt | ggtggtaaat | ttgtcgatgg | 900 |
| aatgaatatc | attggtctgg | tggtggcatc | gattgtattc | ggaatagcac | ttggagcact | 960 |
| gaaagaagat | gtccaactag | tactgaagtt | cttcaacag | ttgtcacata | ccatcatgaa | 1020 |
| agttacagga | tgggttatat | ggttgtcgcc | catcggagtg | ttgtttttga | ttactgccaa | 1080 |
| actgttggaa | atgaagatc | taggagccgt | cttcggtaaa | ctaggtctat | actttgccgt | 1140 |
| agttgctggt | ggaattgtat | tccacggatt | cgtcattctt | ccgctgttgt | tcttcctgtt | 1200 |
| cactcgtaaa | aatccagtca | aatttgtagc | aaacatgggt | caagcgattg | ccaccgcctt | 1260 |
| cggaacctcg | tcaagttcgg | cgaccttgcc | agtgactatg | caatgcctcg | aagacaaaaa | 1320 |

-continued

```
tcacatcgat ccacgtgtgt cccgatttgt gctaccgatt ggtgccacta tcaatatgga    1380
cggcactgcc ttgtacgaag ctgtggccgc cattttcatt gctcaactca gaggactttc    1440
gctcacattt gggaacatag ttgccataag cataacagcg acagcagcca gcataggcgc    1500
agcaggaatt cctcaggccg gattagtcac attggtcatg gtgctggata cagttggtct    1560
accagcagaa gacgtatcac tcataatagc cgtggattgg ttgttggatc gcttccgcac    1620
cgtggtaaac gtgctgggag atagctttgg tgcggccatt gtcgcccact acagtcaaaa    1680
ggaactgaca acaattccat ccagtgagat taacgggaaa actcaacgaa attctctggt    1740
gcacagtgct gagacagtgg tattcgaaga gaggctgtaa gcgaaactga tgaccacttt    1800
ttgatttaag catgttaata actcgtactg agtagatgac tcgatcttaa cgtaaaaact    1860
aaggcaacca tgtcaaagta aagtgttatg ttattgaaaa attaaccgta ttaacttatg    1920
atgtaaggta actgcaaaca ttgatattga atgaaataaa cgttatcctc aacaacaaga    1980
aaaaaaaaaa aaaaa                                                      1995
```

<210> SEQ ID NO 8
<211> LENGTH: 481
<212> TYPE: PRT
<213> ORGANISM: Aedes aegypti
<220> FEATURE:
<223> OTHER INFORMATION: glutamate transporter

<400> SEQUENCE: 8

```
Met Arg Arg Glu Gln Leu Gln Ala Phe Val Lys Glu Asn Leu Leu Thr
  1               5                  10                  15

Phe Leu Thr Ile Gly Gly Val Ile Val Gly Ile Val Leu Gly Ile Gly
                 20                  25                  30

Leu Arg Glu Val Pro Ala Glu Gly Glu Lys Trp Thr Ala Arg Asp Val
             35                  40                  45

Ala Tyr Ile Asn Phe Val Gly Asp Ile Phe Leu Arg Met Leu Lys Ala
         50                  55                  60

Leu Ile Leu Pro Leu Ile Val Thr Ser Leu Ile Ala Ala Val Gly Ser
 65                  70                  75                  80

Leu Asp Leu Ser Leu Ser Gly Lys Ile Gly Gly Arg Ala Val Leu Tyr
                 85                  90                  95

Tyr Val Ile Thr Thr Val Met Ala Val Ile Leu Gly Ile Val Leu Val
            100                 105                 110

Val Thr Ile Gln Pro Gly Lys Gly Ala Glu Glu Thr Ser Gly Ala Val
            115                 120                 125

Lys Gly Glu Val Arg Asn Val Thr Thr Ala Asp Thr Leu Leu Asp Leu
        130                 135                 140

Val Arg Asn Met Phe Pro Pro Asn Leu Val Gln Ala Cys Leu Gln Gln
145                 150                 155                 160

Tyr Gln Thr Val Leu Thr Pro Pro Lys Ser Asn Pro Val Glu Thr Asp
                165                 170                 175

Leu Ile Leu Trp Ser Val Gly Gly Lys Phe Val Asp Gly Met Asn Ile
            180                 185                 190

Ile Gly Leu Val Val Ala Ser Ile Val Phe Gly Ile Ala Leu Gly Ala
        195                 200                 205

Leu Lys Glu Asp Val Gln Leu Val Leu Lys Phe Phe Gln Gln Leu Ser
    210                 215                 220

His Thr Ile Met Lys Val Thr Gly Trp Val Ile Trp Leu Ser Pro Ile
225                 230                 235                 240
```

-continued

```
Gly Val Leu Phe Leu Ile Thr Ala Lys Leu Leu Glu Met Glu Asp Leu
                245                 250                 255
Gly Ala Val Phe Gly Lys Leu Gly Leu Tyr Phe Ala Val Val Ala Gly
            260                 265                 270
Gly Ile Val Phe His Gly Phe Val Ile Leu Pro Leu Leu Phe Phe Leu
        275                 280                 285
Phe Thr Arg Lys Asn Pro Val Lys Phe Val Ala Asn Met Gly Gln Ala
290                 295                 300
Ile Ala Thr Ala Phe Gly Thr Ser Ser Ser Ala Thr Leu Pro Val
305                 310                 315                 320
Thr Met Gln Cys Leu Glu Asp Lys Asn His Ile Asp Pro Arg Val Ser
                325                 330                 335
Arg Phe Val Leu Pro Ile Gly Ala Thr Ile Asn Met Asp Gly Thr Ala
            340                 345                 350
Leu Tyr Glu Ala Val Ala Ala Ile Phe Ile Ala Gln Leu Arg Gly Leu
        355                 360                 365
Ser Leu Thr Phe Gly Asn Ile Val Ala Ile Ser Ile Thr Ala Thr Ala
370                 375                 380
Ala Ser Ile Gly Ala Ala Gly Ile Pro Gln Ala Gly Leu Val Thr Leu
385                 390                 395                 400
Val Met Val Leu Asp Thr Val Gly Leu Pro Ala Glu Asp Val Ser Leu
                405                 410                 415
Ile Ile Ala Val Asp Trp Leu Leu Asp Arg Phe Arg Thr Val Val Asn
            420                 425                 430
Val Leu Gly Asp Ser Phe Gly Ala Ala Ile Val Ala His Tyr Ser Gln
        435                 440                 445
Lys Glu Leu Thr Thr Ile Pro Ser Ser Glu Ile Asn Gly Lys Thr Gln
450                 455                 460
Arg Asn Ser Leu Val His Ser Ala Glu Thr Val Val Phe Glu Glu Arg
465                 470                 475                 480
Leu
```

<210> SEQ ID NO 9
<211> LENGTH: 4956
<212> TYPE: DNA
<213> ORGANISM: Manduca sexta
<220> FEATURE:
<223> OTHER INFORMATION: neurotransmitter transporter encoded by
    inebriated gene

<400> SEQUENCE: 9

```
ccacgcgtcc gcagtcggtt ggccaactaa accgacctcg ctcgctctcg cgtccgttca      60
ttattcacag tcgcgcgtcg tcagcggcgc acgcgactaa tagtcaccgc gtcatgaccc     120
tgtaacgtga tagcatgaat aaagtcgaat cttcgacgga agccgccgcg cccagcgtgg     180
caatccacgt ggaacaacat gacgacgaac aggacaaaga gaactccaag ttactctcgg     240
cgcactcacc ggcacccagc ataacccat cggggcaaat gcgaaaagta aagagtttca     300
gtgatacaca caagatacga gatgtgacca ctgcttcagg cgcagcgtcg gcgcggagtc     360
tgcgtcctta cgaaatagtg aacacgtatc ccgagggatc agaaagtgga actaacaatt     420
atggagcacc gtccgtccgg tcgcttgctt ccatcggaat gggttgtacg gacgacgta      480
aaatggttat tagacgagta ccaacatcgc ccacggaatt gttccatcta gttcgtcctc     540
ctacgcctcc cgacgaagat tcggcgtcgc acgaaagtga ttgcgaggaa gaagaagaag     600
atgctgcggt tcacctcaag ccacgcaggc ccttctgggc caacaagata cagttcgtgc     660
```

```
tggcttgcgt gggatattcc gtcggcctcg gcaacgtgtg gcgcttccct tatctctgct    720
acaaaagtgg aggaggggca ttcctcattc catacttcat cattctatta atttgcggcg    780
tgccaatgct cttcatggaa ctcgccatag gacagtatac agcacacggc cctattgggg    840
ctctatcaca aatttgtcca cttttttaaag gcgctggctt agcaagtgtg gtgatctcat   900
ttctaatgtc cacgtattac gctgtgataa ttgcatgggc catatattat tttttcacat    960
cattcaaaac cgaagtacct tgggcaagtt gctccaatcg atggaacaca gaccaatgct   1020
gggttccaaa tcacaaccat acgaaaccga acggatcaca acacccacc gaacaatttt    1080
tcgagagaaa ggtattgaat atgagtgctg gtattgagta tcctggtggc atgcggtggg   1140
aattggcagc ttgcttggtc tgtgcttggg tgttagttta tttcgccct tggaaaagca    1200
ttaaatcttc agccaaagtt cgttatatca caacaacact gccatttctg ctgattatag   1260
tctttcttgg acgtctttg acactcgatg gagcagatgg aggcttgagg ttcttcttta    1320
aaccagactg ggaacttta aaacagtcca ggccttgggt caacgctgcg tcacagatct    1380
ttaactctat cggaatagca ttcgggtcga tgatcatgtt cgcttcttac aaccgattcg   1440
acaacaactt cctgcacgat accgtagccg tcactctagt caacgctatt actagtctca   1500
tagttggcat attcaccttt gctaccatcg gaaatatcgc cttcgaacaa aatactcccg   1560
tgaaggatgt catagccgac agtccaggcc tattatttgt agtgtacccg caagctatag   1620
caaaaatgcc agcatctcag ctatgggcag tactgttctt cttcatgttt ctatgccttg   1680
gattaaatag tcaatttgct atagtggaag tggtcgtgac ttcaatacaa gacggatttc   1740
ccgacatgat acgaaaaaga cttgtgtatc atgaattatt agtactgctt gtgtgtgcgg   1800
tgtcattatt atgcggactg ccacacatta ttcatagcgg tatatatgta ttccagttaa   1860
tggattatta cgccgcgtcg ctcagtataa cttatctcgc cttttttgag gtggtcgcga   1920
ttgcatggtt ttatgcgtg ggaagactgt ctagaaatat taaacaaatg acaggtcgcc    1980
aaccatcgct atactttcga ttctgttggc tgatagcgtc accggcgctg ctgttagcgt   2040
tgtgggtggc aagcatggtc gactacacgc cgcctagtta caggcagtac caatatcccg   2100
catgggcaca agctctcgga tggatcatgg cttccctctc cttactttgc atcccagtat   2160
acgcggttat agtataatt agagcacctg gagacagttt aagagagaaa ctacgttact    2220
caatacaacc aacatctata tgtgaatgtg gtgtaaatgg ctgtgacatc tgctgctctg   2280
agtcggatcc gccggacgac aaaacagtta ttaattagta taatgaaacc gtatatttta   2340
aagagtatta ttaaaaatga taagaattaa gtactccctc tgccacgagg aacaaataac   2400
atttgggcct gcgttcttta tgacgatata gattcaacac ggtatgtttg taacgaataa   2460
tcaagtttaa taaggacata taaaattaag taactggcat atacccagaa atctatttag   2520
tcatactgaa tccatgttca gggcgctgac caatttctta tcgatttttt gattcgcacc   2580
tgtgtaatcg acaaagtttg tcatcgaaaa ttaccgtcta aagagggtac tcgtgataaa   2640
caatactacg tagataattt acaacgatct tccatcataa gtacacatca ctcgacctcg   2700
acctacaatt atgagcattc accaaacagt gtcatgacat ataactat ggtcatataa     2760
attttataca gttacaatgt aggagtgaaa atcatgtatg tacttctgac gtcgcgcgat   2820
aatgcattga cttcgatagt ataaatagca tttaaatcat atcattacaa agaaatacac   2880
ctattgttat atattttac tatgcacata ttaaaaacta tgtgttagcg gtaactgtgt    2940
tctgtgtagg tattcataat agcagaaatg tattattact gaatgtttgt aaagctttat   3000
```

```
attctcccag tcacgatatt atattgcata agtatgtaaa tatgtaattt aaggcccgac   3060
caccagcaaa ccagagctta acagattctt agaagccatt tatccaaatt tataacatac   3120
taaaaaaaat atttaaataa tttaagaaat atttaaaaga catatttttg caatgtgtta   3180
tctttatttt aattgtataa aatttttata atagaatatt gtttcgttaa tttcattgtg   3240
aaaatgcaat taaaattgtt gactccgtgc attttctcat aaacatgaat caagtactct   3300
aacactatta gaaagacaat tttataaaga atatttttgt agttcctatt taaattttt    3360 tttttgaatg aactatcgta aatctttgca atttggcgcc ggtaacttgc gcgctgccaa   3420
gttcctataa aacgaatcgc tcaaggacgt ttgctagggg agggaccttga cataatggtc  3480 tgttttatag gctggtctac aacctagtaa tacctatgta gtgttgaaac accgaataaa   3540
ttattttaat cgttgtggaa atttgtgtag atccttaccg ataaagattt caaataact    3600 tcccggtaaa attatgtagg tatacagtga aatttgatta aagtgagcct tggacaatat   3660
atgagaaacc actgctaata ataattgcaa taaggtcccg gtacttttgc attaagcctc   3720
ttttactggg aatttcaaac ctcgttaatt gagaatcgat ttcttagatt ttacgatgtt   3780
catctctata attgagactt ggtaggtcaa tcacctatat cagtaaaaca atttatcagg   3840
tttggtaagg ttacgactcg tttgtataca aatattttaa ttacttctgc acatttttaa   3900
ccactcttgt catctatctc tataaataag acaactgtca ttgcaaacct ccctatttgt   3960
atactggcta ataaaaatg ctctatacaa atcctaactc ctttgagatc ccagttaaat    4020
agttgtatag atttcactgt attatacatt tctagccatt tttatgtcaa tgttcatgtt   4080
attgaataat cggcgataaa catcctcaaa tcgtaggaca taaataagct atacgattta   4140
catatacact agtaatatgt agcaacaaca taaaccttg agggcatcag tattaatttt    4200
taagttaagt atcaggcctt ttatattatt ttatttttcct aaaaggataa atatttaatc  4260
atatttgtaa ccatcgaccg tacttgcata ggtatataat atatatttgt tgtgttgtaa   4320
gattgttttt cctgaataat gtgaccgaaa acattccata aatacctata ctcatgtaat   4380
ttaaagatag ttttaatatt tttagatagt tatttatttt gcataccttga taaaacatgg   4440 atgttaagaa tatgtaagca aattgtatta cttaagtaac tatctcagta aataggtagg   4500
ttgccacaga aattgtaatt tttcgtcaat cactaaaata aaatgactgc ttagccgtga   4560
gcatagccgg gggggcaac gttaggcggc acccacccta taagcccctgc gttacctctg   4620 taacgatgtc tctacatcgc gtgatacagg ccttttttaaa atcagcgggt ttttcctcg    4680 ccagcggtct cttcctagat aaaatccgta gctacgccaa ccttccgagt actaaacaaa   4740
acatgaaaca atatttttg ttgttatctg ccactgatat agaatcttac atacctacgt    4800
aaaatcagtc ttttgaaaag taaatcgttc ataattatta tagtgtaaat aggtacattt   4860
tttgtatata agtaaaataa gtaacggcaa ggtatcataa ggcaaaagcg aaataaagtc   4920
ctaaggttaa tgagcaaaaa aaaaaaaaaa aaaaaa                             4956
```

<210> SEQ ID NO 10
<211> LENGTH: 727
<212> TYPE: PRT
<213> ORGANISM: Manduca sexta
<220> FEATURE:
<223> OTHER INFORMATION: neurotransmitter transporter encoded by
      inebriated gene

<400> SEQUENCE: 10

Met Asn Lys Val Glu Ser Ser Thr Glu Ala Ala Ala Pro Ser Val Ala
 1               5                  10                  15

-continued

```
Ile His Val Glu Gln His Asp Asp Glu Gln Asp Lys Glu Asn Ser Lys
            20                  25                  30

Leu Leu Ser Ala His Ser Pro Ala Pro Ser Ile Thr Pro Ser Gly Gln
        35                  40                  45

Met Arg Lys Val Lys Ser Phe Ser Asp Thr His Lys Ile Arg Asp Val
    50                  55                  60

Thr Thr Ala Ser Gly Ala Ala Ser Ala Arg Ser Leu Arg Pro Tyr Glu
65                  70                  75                  80

Ile Val Asn Thr Tyr Pro Glu Gly Ser Glu Ser Gly Thr Asn Asn Tyr
                85                  90                  95

Gly Ala Pro Ser Val Arg Ser Leu Ala Ser Ile Gly Met Gly Cys Thr
            100                 105                 110

Asp Gly Arg Lys Met Val Ile Arg Arg Val Pro Thr Ser Pro Thr Glu
        115                 120                 125

Leu Phe His Leu Val Arg Pro Pro Thr Pro Pro Asp Glu Asp Ser Ala
    130                 135                 140

Ser His Glu Ser Asp Cys Glu Glu Glu Glu Asp Ala Ala Val His
145                 150                 155                 160

Leu Lys Pro Arg Arg Pro Phe Trp Ala Asn Lys Ile Gln Phe Val Leu
                165                 170                 175

Ala Cys Val Gly Tyr Ser Val Gly Leu Gly Asn Val Trp Arg Phe Pro
            180                 185                 190

Tyr Leu Cys Tyr Lys Ser Gly Gly Gly Ala Phe Leu Ile Pro Tyr Phe
        195                 200                 205

Ile Ile Leu Leu Ile Cys Gly Val Pro Met Leu Phe Met Glu Leu Ala
    210                 215                 220

Ile Gly Gln Tyr Thr Ala His Gly Pro Ile Gly Ala Leu Ser Gln Ile
225                 230                 235                 240

Cys Pro Leu Phe Lys Gly Ala Gly Leu Ala Ser Val Val Ile Ser Phe
                245                 250                 255

Leu Met Ser Thr Tyr Tyr Ala Val Ile Ile Ala Trp Ala Ile Tyr Tyr
            260                 265                 270

Phe Phe Thr Ser Phe Lys Thr Glu Val Pro Trp Ala Ser Cys Ser Asn
        275                 280                 285

Arg Trp Asn Thr Asp Gln Cys Trp Val Pro Asn His Asn His Thr Lys
    290                 295                 300

Pro Asn Gly Ser Gln Thr Pro Thr Glu Gln Phe Phe Glu Arg Lys Val
305                 310                 315                 320

Leu Asn Met Ser Ala Gly Ile Glu Tyr Pro Gly Gly Met Arg Trp Glu
                325                 330                 335

Leu Ala Ala Cys Leu Val Cys Ala Trp Val Leu Val Tyr Phe Ala Leu
            340                 345                 350

Trp Lys Ser Ile Lys Ser Ala Lys Val Arg Tyr Ile Thr Thr Thr
        355                 360                 365

Leu Pro Phe Leu Leu Ile Ile Val Phe Leu Gly Arg Ser Leu Thr Leu
    370                 375                 380

Asp Gly Ala Asp Gly Gly Leu Arg Phe Phe Lys Pro Asp Trp Glu
385                 390                 395                 400

Leu Leu Lys Gln Ser Arg Pro Trp Val Asn Ala Ala Ser Gln Ile Phe
                405                 410                 415

Asn Ser Ile Gly Ile Ala Phe Gly Ser Met Ile Met Phe Ala Ser Tyr
            420                 425                 430
```

-continued

```
Asn Arg Phe Asp Asn Asn Phe Leu His Asp Thr Val Ala Val Thr Leu
        435                 440                 445
Val Asn Ala Ile Thr Ser Leu Ile Val Gly Ile Phe Thr Phe Ala Thr
    450                 455                 460
Ile Gly Asn Ile Ala Phe Glu Gln Asn Thr Pro Val Lys Asp Val Ile
465                 470                 475                 480
Ala Asp Ser Pro Gly Leu Leu Phe Val Val Tyr Pro Gln Ala Ile Ala
                485                 490                 495
Lys Met Pro Ala Ser Gln Leu Trp Ala Val Leu Phe Phe Met Phe
            500                 505                 510
Leu Cys Leu Gly Leu Asn Ser Gln Phe Ala Ile Val Glu Val Val Val
        515                 520                 525
Thr Ser Ile Gln Asp Gly Phe Pro Asp Met Ile Arg Lys Arg Leu Val
    530                 535                 540
Tyr His Glu Leu Leu Val Leu Val Cys Ala Val Ser Leu Leu Cys
545                 550                 555                 560
Gly Leu Pro His Ile Ile His Ser Gly Ile Tyr Val Phe Gln Leu Met
                565                 570                 575
Asp Tyr Tyr Ala Ala Ser Leu Ser Ile Thr Tyr Leu Ala Phe Phe Glu
            580                 585                 590
Val Val Ala Ile Ala Trp Phe Tyr Gly Val Gly Arg Leu Ser Arg Asn
        595                 600                 605
Ile Lys Gln Met Thr Gly Arg Gln Pro Ser Leu Tyr Phe Arg Phe Cys
    610                 615                 620
Trp Leu Ile Ala Ser Pro Ala Leu Leu Leu Ala Leu Trp Val Ala Ser
625                 630                 635                 640
Met Val Asp Tyr Thr Pro Pro Ser Tyr Arg Gln Tyr Gln Tyr Pro Ala
                645                 650                 655
Trp Ala Gln Ala Leu Gly Trp Ile Met Ala Ser Leu Ser Leu Leu Cys
            660                 665                 670
Ile Pro Val Tyr Ala Val Ile Val Ile Arg Ala Pro Gly Asp Ser
        675                 680                 685
Leu Arg Glu Lys Leu Arg Tyr Ser Ile Gln Pro Thr Ser Ile Cys Glu
    690                 695                 700
Cys Gly Val Asn Gly Cys Asp Ile Cys Cys Ser Glu Ser Asp Pro Pro
705                 710                 715                 720
Asp Asp Lys Thr Val Ile Asn
                725
```

<210> SEQ ID NO 11
<211> LENGTH: 2034
<212> TYPE: DNA
<213> ORGANISM: Manduca sexta
<220> FEATURE:
<223> OTHER INFORMATION: orphan transporter

<400> SEQUENCE: 11

```
atggcggcca aagctgagcc tattggaccc cgtaatggac acgagttggc gccgttgacc      60
actcgttctg atggctctga aaggcctcat ggtgttacta tcgttcttca aggatcacga     120
gggtccttgc aacgtgatgc tcctgaggaa gaccgcgctg cgtggtcagg gaagctccag     180
tttttcctgt ccatcattgg gtattcggtc ggcctgggca atatatggcg attcccgtat     240
ttgtgtcaac aaaatggcgg cggtgccttc ctaatcccgt tcctcatcat gttggtgctg     300
gaaggcatcc cgctcttcct gatcgagatg gccatcggtc agaagatgcg cctgggctcc     360
```

-continued

```
ctcggagtgt ggaacaccat ccacccatgg ctcggcggca tcggcatctc cagttgcgtg      420
gtgacactct tcgtggctct ttactataac gtgatcatca cttgggtgtt tttctatctc      480
ttcaatagta tacggttaac agccgatcaa ctaccatggg ctcattgccc ttacgacaac      540
ggtacagccg aggctgaatg caacaaggcc tctgccacgg tctacttctg gtaccgcgag      600
gccctggatg cctccccag catcgatgag ccgggcgtgc cgcggtggtg gatagtactc       660
tacctcctgc tggcttggat catcgtgttc ttcattgtga tgaaggggat ccagagtagt      720
gggaaggtgg tttacttcac atctctgttc ccttacgcgg tgctgacgat cttcttcgtg      780
cgcggcatca cgttgcccgg ctcttccgat gggatcctgc acatgtataa acctaagctg      840
gagaaacttc tagacccaac ggtgtgtggc tggacgcggc ttacacaagt gttctactcc      900
ttcgggctcg cgttcggctc cctcatcgcc ttcggctcct ataaccctcc gaacaataac      960
tgcgtgaggg atgtcctcct ggtctccgtg tgtaacgccc taacagcgat ctacgcgtcc     1020
gtggtcatct tcagcatcct cggcttcaag gcttatacca tggtggagaa ctgtattgtc     1080
aaggagatta agtcctagc cctgcatcat atcgggggct tcacgctcaa ctccacggca      1140
gattactatc gggagcagtt cccgagactg aacggtacgg ccatagcagc cctcaacctc     1200
actggatgca ccatgagtcg gcagcttgag gaggcagctg aaggcacggg gctagctttc     1260
atagtgttca cgcaggctat tctgaagctt acaccagctc ctttctggtc catcatattc     1320
ttcctcatgc tgctgtctct gggccttgga agccagatcg gcatcatgga aggaatgctg     1380
tgcaccatct ttgatatcga cttcttcaag aggctgagca agccagttat cactggcgtg     1440
gtctgcactt tctgtttctt cgtggggctc atcttcacga ccggcgcggg agagtactgg     1500
ttgaagatgt tcgactcgtt cgccggcact attggtctcg tcgtcgtcgc tctgctaaag     1560
atgatcgctg ttatttacat ctatggacat gagaagttta caaacgacat ctacgagatg     1620
actggctacc gccccggcat ctactggcaa gtgacgtggc gctacgtggg ccccgccatc     1680
gtcacctgca tcctgctctc gtccctcgtg ttcatgctca tcaacccgcc catgtacggc     1740
gcttggaatg ctgacgaggg tcgcgtcatt aagacaccct acccaacctg gtgtgttggtg    1800
atcgctgtct tgatgatcct ggctggcgtg ctgccaattc cagtggtttt gctgctgcga     1860
aggttccagt gtctcgcctt cgacgttgac atccaccagg gctccatcag gaggattgag     1920
accaccgtct ccactaagga gatgatgagt gatcaggata acgtggagag cagcgaggag     1980
cgccccaaca agcgcctgcc cgccggcatc gcgcgcagtc gccccaagaa ataa           2034
```

<210> SEQ ID NO 12
<211> LENGTH: 676
<212> TYPE: PRT
<213> ORGANISM: Manduca sexta
<220> FEATURE:
<223> OTHER INFORMATION: orphan transporter

<400> SEQUENCE: 12

```
Met Ala Ala Lys Ala Glu Pro Ile Gly Pro Arg Asn Gly His Glu Leu
 1               5                  10                  15

Ala Pro Leu Thr Thr Arg Ser Asp Gly Ser Glu Arg Pro His Gly Val
            20                  25                  30

Thr Ile Val Leu Gln Gly Ser Arg Gly Ser Leu Gln Arg Asp Ala Pro
        35                  40                  45

Glu Glu Asp Arg Ala Ala Trp Ser Gly Lys Leu Gln Phe Phe Leu Ser
    50                  55                  60

Ile Ile Gly Tyr Ser Val Gly Leu Gly Asn Ile Trp Arg Phe Pro Tyr
```

-continued

```
           65                  70                  75                  80
Leu Cys Gln Gln Asn Gly Gly Ala Phe Leu Ile Pro Phe Leu Ile
                    85                  90                  95
Met Leu Val Leu Glu Gly Ile Pro Leu Val Leu Ile Glu Met Ala Ile
                100                 105                 110
Gly Gln Lys Met Arg Leu Gly Ser Leu Gly Val Trp Asn Thr Ile His
            115                 120                 125
Pro Trp Leu Gly Gly Ile Gly Ile Ser Ser Cys Val Thr Leu Phe
        130                 135                 140
Val Ala Leu Tyr Tyr Asn Val Ile Ile Thr Trp Val Phe Phe Tyr Leu
145                 150                 155                 160
Phe Asn Ser Ile Arg Leu Thr Ala Asp Gln Leu Pro Trp Ala His Cys
                165                 170                 175
Pro Tyr Asp Asn Gly Thr Ala Glu Ala Glu Cys Asn Lys Ala Ser Ala
                180                 185                 190
Thr Val Tyr Phe Trp Tyr Arg Glu Ala Leu Asp Ala Ser Pro Ser Ile
            195                 200                 205
Asp Glu Pro Gly Val Pro Arg Trp Trp Ile Val Leu Tyr Leu Leu Leu
        210                 215                 220
Ala Trp Ile Ile Val Phe Phe Ile Val Met Lys Gly Ile Gln Ser Ser
225                 230                 235                 240
Gly Lys Val Val Tyr Phe Thr Ser Leu Phe Pro Tyr Ala Val Leu Thr
                245                 250                 255
Ile Phe Phe Val Arg Gly Ile Thr Leu Pro Gly Ser Ser Asp Gly Ile
                260                 265                 270
Leu His Met Tyr Lys Pro Lys Leu Glu Lys Leu Leu Asp Pro Thr Val
            275                 280                 285
Trp Leu Asp Ala Ala Thr Gln Val Phe Tyr Ser Phe Gly Leu Ala Phe
        290                 295                 300
Gly Ser Leu Ile Ala Phe Gly Ser Tyr Asn Pro Asn Asn Asn Cys
305                 310                 315                 320
Val Arg Asp Val Leu Leu Val Ser Val Cys Asn Ala Leu Thr Ala Ile
                325                 330                 335
Tyr Ala Ser Val Val Ile Phe Ser Ile Leu Gly Phe Lys Ala Tyr Thr
                340                 345                 350
Met Val Glu Asn Cys Ile Val Lys Glu Ile Lys Val Leu Ala Leu His
            355                 360                 365
His Ile Gly Gly Phe Thr Leu Asn Ser Thr Ala Asp Tyr Tyr Arg Glu
        370                 375                 380
Gln Phe Pro Arg Leu Asn Gly Thr Ala Ile Ala Ala Leu Asn Leu Thr
385                 390                 395                 400
Gly Cys Thr Met Ser Arg Gln Leu Glu Glu Ala Ala Glu Gly Thr Gly
                405                 410                 415
Leu Ala Phe Ile Val Phe Thr Gln Ala Ile Leu Lys Leu Thr Pro Ala
                420                 425                 430
Pro Phe Trp Ser Ile Ile Phe Phe Leu Met Leu Leu Ser Leu Gly Leu
            435                 440                 445
Gly Ser Gln Ile Gly Ile Met Glu Gly Met Leu Cys Thr Ile Phe Asp
        450                 455                 460
Ile Asp Phe Phe Lys Arg Leu Ser Lys Pro Val Ile Thr Gly Val Val
465                 470                 475                 480
Cys Thr Phe Cys Phe Phe Val Gly Leu Ile Phe Thr Thr Gly Ala Gly
                485                 490                 495
```

```
Glu Tyr Trp Leu Lys Met Phe Asp Ser Phe Ala Gly Thr Ile Gly Leu
            500                 505                 510
Val Val Val Ala Leu Leu Lys Met Ile Ala Val Ile Tyr Ile Tyr Gly
            515                 520                 525
His Glu Lys Phe Thr Asn Asp Ile Tyr Glu Met Thr Gly Tyr Arg Pro
            530                 535                 540
Gly Ile Tyr Trp Gln Val Thr Trp Arg Tyr Val Gly Pro Ala Ile Val
545                 550                 555                 560
Thr Cys Ile Leu Leu Ser Ser Leu Val Phe Met Leu Ile Asn Pro Pro
                565                 570                 575
Met Tyr Gly Ala Trp Asn Ala Asp Glu Gly Arg Val Ile Lys Thr Pro
            580                 585                 590
Tyr Pro Thr Trp Val Leu Val Ile Ala Val Leu Met Ile Leu Ala Gly
            595                 600                 605
Val Leu Pro Ile Pro Val Val Leu Leu Arg Phe Gln Cys Leu
            610                 615                 620
Ala Phe Asp Val Asp Ile His Gln Gly Ser Ile Arg Arg Ile Glu Thr
625                 630                 635                 640
Thr Val Ser Thr Lys Glu Met Met Ser Asp Gln Asp Asn Val Glu Ser
                645                 650                 655
Ser Glu Glu Arg Pro Asn Lys Arg Leu Pro Ala Gly Ile Ala Arg Ser
            660                 665                 670
Arg Pro Lys Lys
        675

<210> SEQ ID NO 13
<211> LENGTH: 3513
<212> TYPE: DNA
<213> ORGANISM: Manduca sexta
<220> FEATURE:
<223> OTHER INFORMATION: GABA transporter

<400> SEQUENCE: 13
ccacgcgtcc ggcggtgcgc ttgcgacaac acctcctcgg cgatattgtg acggctttcg      60
gtctgtgatg tgttgtgttg tggattgtga tggtttttga tattcaaaat tagcaacggc     120
ccaatttcta gtcaacgtac ttctttaaac atgttggtac attccaccta agtcaaaaat     180
aaattgggat agcggtccag tgtgctgaag aaatttttata aaggtttcga agagataaaa     240
cgagaaggag acatggaaac aaaaaatgat tcacgaagcg acgacatcga acttagcgcg     300
caaggcagcg gtaacaaacc gagcgatgtc gcagtcaaat caaatttacc cgaaagaggc     360
tcctgggcca gcaaactcga cttcatcctc tctgtcatcg gcttggcgat cggtcttggc     420
aatgtctggc gttttcctta cctctgctac aagaacggtg gtggtgcctt cctcatccct     480
tacttcttga ctctcttcct cgctggtatt ccgatgttct tcatgaact  cgctatggga     540
cagatgttga ctatcggagg acttggtgtg ttcaagatcg cccctatttt caaaggtatc     600
ggttatgctg cagctgtcat gtcctgctgg atgaacgtgt actacatagt tatccttgct     660
tgggccatct tctatttctt catgtccatg agatcagatg tcccctggag gaactgcgac     720
aactattgga acacagccac ttgcgtcaac ccctacgata ggaagaacct tacatgctgg     780
tcctcgctgg gcgatatgag caccttctgc accctgaacg gaaggaatgt tagcaaagct     840
gtcctctccg accccgttaa ggaattctgg gaacgccgcg ctcttcaaat ctcttctgga     900
attgaacaca tcggcaacat ccgctgggag ctggcgggga ctctgcttct tgtctgggtt     960
```

-continued

```
ctgtgctact tctgcatctg aagggtgtc aggtggaccg gcaaggtcgt ttacttcacc    1020
gccttgttcc catacttctt gctcactgtt ctgctgatca gaggaattac cctccccgga    1080
gcgatggaag gcattaagtt ctacgtaatg cccaatatgt cgaaactcct ggagtctgaa    1140
gtgtggatcg atgctgtcac tcagatcttc ttctcttatg gccttggttt gggcacactc    1200
gtcgctttgg gaagctacaa caagttcacg aataatgttt acaaagacgc tttgatagtc    1260
tgctcggtga actccagtac ttctatgttc gctggtttcg tgatcttctc cgtggtcggg    1320
ttcatggcgc atgagcagca acggccagtt gctgaggttg ccgcatcagg tcctggctta    1380
gccttcctcg cgtacccatc agcagttctc caacttcccg cgcgctccact ctggtcttgt    1440 ctcttcttct tcatgctgct gctcatcggg ttggatagcc agttctgcac catggaagga    1500
ttcatcaccg ccgtcattga cgagtggccc aaactcctca aaggaggaa ggaaatcttc    1560 atcgccatta cttgcatcat ctcgtacctg gtcggactgt cttgtatatc tgagggtggt    1620
atgtacgtgt tccaaatcct ggactcctac gccgtgtctg gcttctgtct gctgttcctg    1680
atcttcttcg agtgcgtgtc catctcgtgg gcgttcggcg tgaatcgctt ctacgacggt    1740
atcaaggaga tgatcggcta ctaccccacc atttggtgga agttctgctg ggtcggcttc    1800
acgcctgcta tttgtattag cgtcttcatc ttcaacttgg tgcagtggac tccgatcaag    1860
tacatgaact acgaatatcc ctggtggtcc cacgcttttg gctggtttac cgcgctgtcg    1920
tccatgctgt gcatccctgg atacatgatc tacttgtgga gagtcacgcc tggcacttgg    1980
caagagaaat tccacaaaat cgtccgtatt ccggaagatg tgccttctct tcgaaccaag    2040
atgtaggccg aagaacaggc gaaacacgca caaacacgca caggcgtaga cgcagccaac    2100
aacaatgcag gtccaataac ttacaagata tttataacag taagacagaa ttttaaagcc    2160
aatagaagat atataggtaa taaaataact tacaattgtc atgttctctc tgtcattaag    2220
ccgccatatg acagagagag cgtgatatac aaaagacgtt ggacttgcaa agttaacaca    2280
acgacttact taacatcagg atctcaggga gttgagaatt catttggaat gggattcaga    2340
tgtgattatg gtcttgtttc atttgcaaaa ttaatttaa aagttgttaa ctacagacaa    2400
gctttaaaac ttttaataa tcaatatgca tcagtttact ctcaattgtc atcgatattt    2460
atgaaaccat ggaacaaaat tataaggacg tcagtaacgg agtttgatat tctaaatatt    2520
tacgcacaat tagctatcat gtgccaatat cgcagtattt ataatatatt aacctcatgt    2580
tatatttaga tccccgtcta tataaaatcg ggcaaagtag tttatacaat attacgggac    2640
gaatatttgt ggagcgtatt ttctattccc aaatatcttt cctggtccat agtaggacat    2700
attcgtctac gctagtctag atctatgtat gtgattttta gaaaataata atatttaggc    2760
ctaagataat ttgatgactt tccgtttgaa cagtgtgtgc gttgcgacgc gtttacgtat    2820
gtttacattt tacaattatt tataaggttt agattttaag tgaaatatat ttttaattat    2880
tatctgtctt ccatttaact tagtgttaag gttttttgaat ccacgcgtcc ggcggtgcgc    2940
ttgcgacaac acctcctcgg cgatattgtg acggctttcg gtctgtgatg tgttgtgttg    3000
tggattgtga tggtttttga tattcaaaat tagcaacggc ccaatttcta gtcaacgtac    3060
ttctttaaac atgttggtac attccaccta agtcaaaaat aaattgggat agcggtccag    3120
tgtgctgaag aaattttata aaggtttcga agagataaaa cgagaaggag acatggaaac    3180
aaaaaatgat tcacgaagcg acgacatcga acttagcgcg caaggcagcg gtaacaaacc    3240
gagcgatgtc gcagtcaaat caaatttacc cgaaagaggc tcctgggcca gcaaactcga    3300
cttcatcctc tctgtcatcg gcttggcgat cggtcttggc aatgtctggc gttttcctta    3360
```

```
cctctgctac aagaacggtg gtggtgcctt cctcatccct tacttcttga ctctcttcct   3420
cgctggtatt ccgatgttct tcatggaact cgctatggga cagatgttga ctatcggagg   3480
acttggtgtg ttcaagatcg cccctatttt caa                               3513
```

<210> SEQ ID NO 14
<211> LENGTH: 597
<212> TYPE: PRT
<213> ORGANISM: Manduca sexta
<220> FEATURE:
<223> OTHER INFORMATION: GABA transporter

<400> SEQUENCE: 14

```
Met Glu Thr Lys Asn Asp Ser Arg Ser Asp Asp Ile Glu Leu Ser Ala
 1               5                  10                  15

Gln Gly Ser Gly Asn Lys Pro Ser Asp Val Ala Val Lys Ser Asn Leu
            20                  25                  30

Pro Glu Arg Gly Ser Trp Ala Ser Lys Leu Asp Phe Ile Leu Ser Val
        35                  40                  45

Ile Gly Leu Ala Ile Gly Leu Gly Asn Val Trp Arg Phe Pro Tyr Leu
 50                  55                  60

Cys Tyr Lys Asn Gly Gly Ala Phe Leu Ile Pro Tyr Phe Leu Thr
 65                  70                  75                  80

Leu Phe Leu Ala Gly Ile Pro Met Phe Phe Met Glu Leu Ala Met Gly
                85                  90                  95

Gln Met Leu Thr Ile Gly Leu Gly Val Phe Lys Ile Ala Pro Ile
            100                 105                 110

Phe Lys Gly Ile Gly Tyr Ala Ala Ala Val Met Ser Cys Trp Met Asn
        115                 120                 125

Val Tyr Tyr Ile Val Ile Leu Ala Trp Ala Ile Phe Tyr Phe Phe Met
130                 135                 140

Ser Met Arg Ser Asp Val Pro Trp Arg Asn Cys Asp Asn Tyr Trp Asn
145                 150                 155                 160

Thr Ala Thr Cys Val Asn Pro Tyr Asp Arg Lys Asn Leu Thr Cys Trp
                165                 170                 175

Ser Ser Leu Gly Asp Met Ser Thr Phe Cys Thr Leu Asn Gly Arg Asn
            180                 185                 190

Val Ser Lys Ala Val Leu Ser Asp Pro Val Lys Glu Phe Trp Glu Arg
        195                 200                 205

Arg Ala Leu Gln Ile Ser Ser Gly Ile Glu His Ile Gly Asn Ile Arg
    210                 215                 220

Trp Glu Leu Ala Gly Thr Leu Leu Val Trp Val Leu Cys Tyr Phe
225                 230                 235                 240

Cys Ile Trp Lys Gly Val Arg Trp Thr Gly Lys Val Val Tyr Phe Thr
                245                 250                 255

Ala Leu Phe Pro Tyr Phe Leu Leu Thr Val Leu Leu Ile Arg Gly Ile
            260                 265                 270

Thr Leu Pro Gly Ala Met Glu Gly Ile Lys Phe Tyr Val Met Pro Asn
        275                 280                 285

Met Ser Lys Leu Leu Glu Ser Glu Val Trp Ile Asp Ala Val Thr Gln
    290                 295                 300

Ile Phe Phe Ser Tyr Gly Leu Gly Leu Gly Thr Leu Val Ala Leu Gly
305                 310                 315                 320

Ser Tyr Asn Lys Phe Thr Asn Asn Val Tyr Lys Asp Ala Leu Ile Val
                325                 330                 335
```

| Cys | Ser | Val | Asn | Ser | Ser | Thr | Ser | Met | Phe | Ala | Gly | Phe | Val | Ile | Phe |
|     |     |     | 340 |     |     |     | 345 |     |     |     |     | 350 |     |     |     |

| Ser | Val | Val | Gly | Phe | Met | Ala | His | Glu | Gln | Gln | Arg | Pro | Val | Ala | Glu |
|     |     |     | 355 |     |     |     | 360 |     |     |     | 365 |     |     |     |     |

Val Ala Ala Ser Gly Pro Gly Leu Ala Phe Leu Ala Tyr Pro Ser Ala
            370             375             380

Val Leu Gln Leu Pro Gly Ala Pro Leu Trp Ser Cys Leu Phe Phe
385             390             395             400

Met Leu Leu Leu Ile Gly Leu Asp Ser Gln Phe Cys Thr Met Glu Gly
            405             410             415

Phe Ile Thr Ala Val Ile Asp Glu Trp Pro Lys Leu Leu Arg Arg Arg
            420             425             430

Lys Glu Ile Phe Ile Ala Ile Thr Cys Ile Ile Ser Tyr Leu Val Gly
            435             440             445

Leu Ser Cys Ile Ser Glu Gly Gly Met Tyr Val Phe Gln Ile Leu Asp
    450             455             460

Ser Tyr Ala Val Ser Gly Phe Cys Leu Leu Phe Leu Ile Phe Glu
465             470             475             480

Cys Val Ser Ile Ser Trp Ala Phe Gly Val Asn Arg Phe Tyr Asp Gly
            485             490             495

Ile Lys Glu Met Ile Gly Tyr Tyr Pro Thr Ile Trp Trp Lys Phe Cys
            500             505             510

Trp Val Gly Phe Thr Pro Ala Ile Cys Ile Ser Val Phe Ile Phe Asn
            515             520             525

Leu Val Gln Trp Thr Pro Ile Lys Tyr Met Asn Tyr Glu Tyr Pro Trp
            530             535             540

Trp Ser His Ala Phe Gly Trp Phe Thr Ala Leu Ser Ser Met Leu Cys
545             550             555             560

Ile Pro Gly Tyr Met Ile Tyr Leu Trp Arg Val Thr Pro Gly Thr Trp
            565             570             575

Gln Glu Lys Phe His Lys Ile Val Arg Ile Pro Glu Asp Val Pro Ser
            580             585             590

Leu Arg Thr Lys Met
        595

```
<210> SEQ ID NO 15
<211> LENGTH: 2529
<212> TYPE: DNA
<213> ORGANISM: Aedes aegypti
<220> FEATURE:
<223> OTHER INFORMATION: LAT transporter

<400> SEQUENCE: 15
tgcaaattca gttcaacgag cgcgacgagc aactgcgaat ccagtttcat tccaagtgcg      60 ataaagtca gttgattcag aaagaacggt aggcgccaaa atggtactga acaacgggg      120 agcggccata gagctacact ctcctacgga ggatgtgctg gtcagtccgg gaaccgagag     180
tttgccaccg atcgaaaatg gagccatcgc cggttccggg acgattgatg gcggcggagg     240
aaacgaacgt gtcaaaatga aaaagaact ggggctgctg gaaggagtgg ccatcatctt      300
gggtattatc ttcggctcgg gaattttcat ctcgccgaag ggtgtgcttc aggaggttgg     360
cgccgtgggg acttcgctgg tcatttgggt gacgtgcggg ttgctgtcga tgattggcgc     420
gctgtgctat gcagaactgg gcacggcgat accgaaatcc ggtggcgatt atgcttacat     480
ttatgaggct tatggcccac ttccggcgtt cctgtatctt tgggacgcaa cggtgatatt     540
```

-continued

```
tgtaccgagt acgaacgcca tcatgggact taccttcgcc agctatgtgt tccaaccgct    600
gttttgcggcc ggatgttccg ttcccacgat agggctgcag ttgtttgccg ccgtgacgat    660
atgtttgctc acgtacatca atgcttacga cgtccgggtg acgaccaaaa tgcagaatgt    720
gttcatgttc accaaaatcg gtgctctggt gctggtcatc atcgttggtg tggtgtggat    780
gtcgctcggt ggaacggaga actttgagaa cgccttcgag aacacggaaa ccgaccccgg    840
caagctggcg gtggcattct attccggtat cttctcgtat gctggatgga attacttgaa    900
cttcatgacg gaggagcttc gtgacccgta caagaacctg ccccgagcga tctacatctc    960
tctcccgttg gtcaccggta tctacgtgct ggccaacatg gcttacgttg cagttctatc   1020
gccgcagcag attctctcat cggatgctat cgccgtgaca ttcgcccaga agccatggg   1080
ctggggtgcc ttcgtgatgc ccatcctggt agctatttcg gccttcggtg tctctccgt   1140
gcacatcatg acctcatcgc gaatgtgctt cgtcggggcc cgcaacggac acatgccgga   1200
gatcctcttc cacatcaacg tcaatcggta cacttcgatg ccgtcgctgg tgttcctctg   1260
cctcctatcg ttgctgtacc tattcatcag cgacgtgtac gtcctgatca cctacagcag   1320
tatcgtcgag tcgttcttca tcatgctctc ggtgagtgcg gttctgtact ccgctacac   1380
ccgaccggac atcaaccggc cgatcaaggt ccaactgtgg gtcccaacgc tgtttgtcat   1440
catctgtgcg ttcctgatcg tggtcccgtg ctacgtggca ccgtacgaag tgggcatggg   1500
tgtcctcctg acgctggccg gtattcccgt gtactacgtc ggtgtggcgt ggaagaacaa   1560
gccggaatcc ttcgagaacg tcctgcgccg ggcgacacag ttctgccaga agatgttcat   1620
gacggccaaa gaggaaaatg atgacgagga atgagaggag catgcccggt aatgtacagc   1680
ttacagtttt aattagtagt gccgacgcaa agtgatagta ggtttgacta ttttttaatt   1740
agttaacgtg accaaacaaa attttttattc tcggacgaaa tttaaatctc aatcgttata   1800
gatctgtttt catcaattga caaaatttta gatcagtgcc aaatatgttt ggagtcgatt   1860
ttggatcata cactcccacg gttttttgtt gcgatgaaat cgcgaaatca ttagtcaaaa   1920
ttgaaaattt actttatgtt tccacatgtg cgtccagttc cagtacttac aatttaagtc   1980
agacaaatca aataaaaatg tactttataa tctccattgc attttgtgta agagtctcca   2040
tcaacgaacc ggaaaccgaa gtgtcccggt ccggtatgat acttcttcat aagaagtcaa   2100
gcaaacgaaa gtgtagaata ttttcactca atcctataat agaccaatga ggtttaagct   2160
aaaaccaata cgcttttgag cttttctcta tcaaacatca caccgatcaa ttagaatctc   2220
atgctcatgc tatatgttgt cggacttgcg gcgccagatt gtaccaagaa ctggtttgat   2280
atctagaagc aaaacatctc actgaaagag ggaaagacaa aagataagac tattatacat   2340
acacaaacac tcgaataaag caaactgctc gtagttagcc gttgaagtta gcatagtgcg   2400
agtatggaag ttttgaatag aaacgtaaga gattgaataa cataggttaa gtttgcaagc   2460
aatgccgaca aatacccatt atgataataa accatgctag attttttgtt aaaaaaaaaa   2520
aaaaaaaa                                                              2529
```

<210> SEQ ID NO 16
<211> LENGTH: 517
<212> TYPE: PRT
<213> ORGANISM: Aedes aegypti
<220> FEATURE:
<223> OTHER INFORMATION: LAT transporter

<400> SEQUENCE: 16

```
Met Val Leu Lys Gln Arg Gly Ala Ala Ile Glu Leu His Ser Pro Thr
 1               5                  10                  15

Glu Asp Val Leu Val Ser Pro Gly Thr Glu Ser Leu Pro Pro Ile Glu
             20                  25                  30

Asn Gly Ala Ile Ala Gly Ser Gly Thr Ile Asp Gly Gly Gly Gly Asn
         35                  40                  45

Glu Arg Val Lys Met Lys Lys Glu Leu Gly Leu Leu Glu Gly Val Ala
     50                  55                  60

Ile Ile Leu Gly Ile Ile Phe Gly Ser Gly Ile Phe Ile Ser Pro Lys
 65                  70                  75                  80

Gly Val Leu Gln Glu Val Gly Ala Val Gly Thr Ser Leu Val Ile Trp
             85                  90                  95

Val Thr Cys Gly Leu Leu Ser Met Ile Gly Ala Leu Cys Tyr Ala Glu
             100                 105                 110

Leu Gly Thr Ala Ile Pro Lys Ser Gly Gly Asp Tyr Ala Tyr Ile Tyr
             115                 120                 125

Glu Ala Tyr Gly Pro Leu Ser Ala Phe Leu Tyr Leu Trp Asp Ala Thr
 130                 135                 140

Val Ile Phe Val Pro Ser Thr Asn Ala Ile Met Gly Leu Thr Phe Ala
145                 150                 155                 160

Ser Tyr Val Phe Gln Pro Leu Phe Ala Ala Gly Cys Ser Val Pro Thr
             165                 170                 175

Ile Gly Leu Gln Leu Phe Ala Ala Val Thr Ile Cys Leu Leu Thr Tyr
             180                 185                 190

Ile Asn Ala Tyr Asp Val Arg Val Thr Thr Lys Met Gln Asn Val Phe
         195                 200                 205

Met Phe Thr Lys Ile Gly Ala Leu Val Leu Val Ile Ile Val Gly Val
     210                 215                 220

Val Trp Met Ser Leu Gly Gly Thr Glu Asn Phe Glu Asn Ala Phe Glu
225                 230                 235                 240

Asn Thr Glu Thr Asp Pro Gly Lys Leu Ala Val Ala Phe Tyr Ser Gly
             245                 250                 255

Ile Phe Ser Tyr Ala Gly Trp Asn Tyr Leu Asn Phe Met Thr Glu Glu
             260                 265                 270

Leu Arg Asp Pro Tyr Lys Asn Leu Pro Arg Ala Ile Tyr Ile Ser Leu
     275                 280                 285

Pro Leu Val Thr Gly Ile Tyr Val Leu Ala Asn Met Ala Tyr Val Ala
     290                 295                 300

Val Leu Ser Pro Gln Gln Ile Leu Ser Ser Asp Ala Ile Ala Val Thr
305                 310                 315                 320

Phe Ala Gln Lys Ala Met Gly Trp Gly Ala Phe Val Met Pro Ile Leu
             325                 330                 335

Val Ala Ile Ser Ala Phe Gly Gly Leu Ser Val His Ile Met Thr Ser
             340                 345                 350

Ser Arg Met Cys Phe Val Gly Ala Arg Asn Gly His Met Pro Glu Ile
     355                 360                 365

Leu Phe His Ile Asn Val Asn Arg Tyr Thr Ser Met Pro Ser Leu Val
     370                 375                 380

Phe Leu Cys Leu Leu Ser Leu Leu Tyr Leu Phe Ile Ser Asp Val Tyr
385                 390                 395                 400

Val Leu Ile Thr Tyr Ser Ser Ile Val Glu Ser Phe Phe Ile Met Leu
             405                 410                 415

Ser Val Ser Ala Val Leu Tyr Phe Arg Tyr Thr Arg Pro Asp Ile Asn
```

-continued

```
                    420             425             430
Arg Pro Ile Lys Val Gln Leu Trp Val Pro Thr Leu Phe Val Ile Ile
        435                 440                 445

Cys Ala Phe Leu Ile Val Val Pro Cys Tyr Val Ala Pro Tyr Glu Val
        450                 455                 460

Gly Met Gly Val Leu Leu Thr Leu Ala Gly Ile Pro Val Tyr Val
465                 470                 475                 480

Gly Val Ala Trp Lys Asn Lys Pro Glu Ser Phe Glu Asn Val Leu Arg
                485                 490                 495

Arg Ala Thr Gln Phe Cys Gln Lys Met Phe Met Thr Ala Lys Glu Glu
        500                 505                 510

Asn Asp Asp Glu Glu
        515

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence:1S forward
      degenerate primer for NTTs (A69)
<221> NAME/KEY: modified_base
<222> LOCATION: (19)
<223> OTHER INFORMATION: n = i
<221> NAME/KEY: modified_base
<222> LOCATION: (25)
<223> OTHER INFORMATION: n = i
<221> NAME/KEY: modified_base
<222> LOCATION: (31)
<223> OTHER INFORMATION: n = g, a, c or t

<400> SEQUENCE: 17
cggaattctg gscaayrtnt ggmgnttycc nta                           33

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence:4A reverse
      degenerate primer for NTTs (A67)
<221> NAME/KEY: modified_base
<222> LOCATION: (24)..(25)
<223> OTHER INFORMATION: n = i
<221> NAME/KEY: modified_base
<222> LOCATION: (28)
<223> OTHER INFORMATION: n = i
<221> NAME/KEY: modified_base
<222> LOCATION: (34)
<223> OTHER INFORMATION: n = g, a, c or t

<400> SEQUENCE: 18
gccaagcttg aagaagatyt grgnngcngc rtcnabcca                     39

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:2S reverse
      degenerate primer for NTTs (A70)
<221> NAME/KEY: modified_base
<222> LOCATION: (16)
<223> OTHER INFORMATION: n = i
<221> NAME/KEY: modified_base
<222> LOCATION: (19)
<223> OTHER INFORMATION: n = i
<221> NAME/KEY: modified_base
```

```
<222> LOCATION: (22)
<223> OTHER INFORMATION: n = i
<221> NAME/KEY: modified_base
<222> LOCATION: (25)
<223> OTHER INFORMATION: n = g, a, c or t

<400> SEQUENCE: 19
ctccatggar aayggnggng gngcntt                                            27

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:3A reverse
      degenerate primer for NTTs (A68)
<221> NAME/KEY: modified_base
<222> LOCATION: (13)
<223> OTHER INFORMATION: n = i
<221> NAME/KEY: modified_base
<222> LOCATION: (16)
<223> OTHER INFORMATION: n = i
<221> NAME/KEY: modified_base
<222> LOCATION: (19)
<223> OTHER INFORMATION: n = i
<221> NAME/KEY: modified_base
<222> LOCATION: (22)
<223> OTHER INFORMATION: n = i
<221> NAME/KEY: modified_base
<222> LOCATION: (25)
<223> OTHER INFORMATION: n = g, a, c or t
<221> NAME/KEY: modified_base
<222> LOCATION: (28)
<223> OTHER INFORMATION: n = g, a, c or t

<400> SEQUENCE: 20
ggcgagctcg gcnccnggna gngtnrcncc                                         30
```

USE OF INSECT CELL MEMBRANE TRANSPORTERS AS NOVEL TARGET SITES FOR INSPECTION

STATEMENT AS TO RIGHTS TO INVENTIONS MADE UNDER FEDERALLY SPONSORED RESEARCH AND DEVELOPMENT

This invention was made with Government support under NIH grant AI34524. The government has certain rights to this invention.

CROSS-REFERENCES TO RELATED APPLICATIONS

Not Applicable.

BACKGROUND OF THE INVENTION

1. Field of the Invention

The present invention relates to a field of insect transporter nucleic acids and proteins, and their use as novel target sites for insecticide development and insecticide action. Recombinant proteins and peptides with insecticidal activity, isolated DNA molecules encoding them, vectors comprising the nucleic acids, and methods of preparing them are provided. Methods of screening for compounds that modulate activity of or bind to membrane transporters are also provided.

2. Description of the Related Art

At present, insecticide resistance is posing serious problems in pest management. Consequently the development of new molecular targets in insect systems is greatly increased.

One method of controlling insect development consists of using biologically active hormones to interfere with insect developmental processes. This method has been used in several insect-based industries, such as in the silk industry. For example, JP 79042912 and JP 50029371 (both to Ajinomoto KK) relate to cultivation of silkworms by feeding with an ecdysis hormone component and juvenile hormone. JP 51013684 (to Takeda) also employs biologically active hormones in combination with contamination controlling agents, as part of a method for preventing internal silkworm contamination. This method, more specifically, provides for treatment with steroid-like molting hormone, juvenile hormone, and antibiotics at specific developmental stages.

Approaches such as the one above suffer several disadvantages, most significantly a relatively limited effectiveness because of the narrow window of susceptibility of insects to these types of steroid-like hormones. On a commercial scale, such agents for insecticidal applications are relatively ineffective, providing for disruption of insect development only at the end of a molt episode.

Insects, including lepidopteran insects, continue to elicit significant loss to many commercially important agricultural crops, including grains (corn, wheat, cotton, soybeans), and various vegetable, fruit (grapes, apples, peaches), and nut crops (almonds, walnuts). Hence, significant economic incentive exists for developing safer and more economic insect controlling strategies.

Conventional insect pest control methods rely primarily on relatively toxic, and non-specific chemical formulations, and have become increasingly unacceptable because of potential toxicities to humans and animals, as well as destruction of desirable plant and animal life. The continued threat such agents pose to the environment add to the growing need for more bio-compatible, specific, yet effective, insect population control techniques. Repeated use of conventional chemical insecticides also enhances the potential for insect resistance, resulting in increased risk of insecticide resistant insect strains and reduced effectiveness.

Alternatively, novel targets for insecticide targets can be identified, such as γ-Aminobutyric acid (GABA). GABA is the primary neurotransmitter in the vertebrate central nervous system and in invertebrate central and peripheral nervous systems. For example, in *Manduca sexta*, GABA has been shown to inhibit neuronal activity, suggesting its involvement in regulating central neural functions in this insect. GABA transporters and other transporters affecting the central nervous system of insects could be used to provide new insecticide targets.

Specifically, insecticides presently available act on only a limited number of target sites and increased insecticide resistance has made many of these targets of limited value. Despite recent advances in the understanding of the biology of insects, a need continues to exist in the art of insect management and control for novel target sites.

SUMMARY OF THE INVENTION

The present invention discloses the existence of novel insect transporters that can be used as targets for screening of new insecticides.

The nucleic acids of this invention encode insect cell membrane transporter polypeptides including acetylcholine transporters, serotonin transporters, proline transporters, glutamate transporters, neurotransmitter transporters encoded by the inebriated gene, orphan transporters, GABA transporters, and LAT transporters. The polypeptides have greater than about 70% amino acid identity to sequences selected from the group consisting of: SEQ ID NOS: 2, 4, 6, 8, 10, 12, 14, and 16.

In one preferred embodiment, the nucleic acids of this invention encode polypeptides with amino acid sequences selected from the group consisting of: SEQ ID NOS: 2, 4, 6, 8, 10, 12, 14, and 16. In another preferred embodiment, the nucleic acids have nucleotide sequences selected from the group consisting of: SEQ ID NOS: 1, 3, 5, 7, 9, 11, 13, and 15.

This invention also provides insect cell membrane transporter polypeptides with greater than 70% amino acid sequence identity to polypeptides with amino acid sequences selected from the group consisting of: SEQ ID NOS: 2, 4, 6, 8, 10, 12, 14, and 16. In another embodiment, this invention provides polypeptides with amino acid sequences selected from the group consisting of: SEQ ID NOS: 2, 4, 6, 8, 10, 12, 14, and 16.

This invention also provides methods of screening for compounds which modulate the activity of insect cell membrane transporters encoded sequences selected from the group consisting of: SEQ ID NOS: 1, 3, 5, 7, 9, 11, 13, and 15 and nucleic acids encoding the amino acid sequences selected from the group consisting of: SEQ ID NOS: 2, 4, 6, 8, 10, 12, 14, and 16. The method comprises the steps of contacting a recombinant cell expressing the insect cell membrane transporter with a test compound and determining the ability of the test compound to modulate the activity of the membrane transporter. In preferred embodiments, the cell membrane transporter has an amino acid sequence selected from the group consisting of: SEQ ID NOS: 2, 4, 6, 8, 10, 12, 14, and 16. This invention also provides a compound identified by the above method.

In yet another embodiment, this invention provides methods of screening for a compound which binds to an insect cell membrane transporter. The method initially comprises attaching a membrane transporter polypeptide with an amino acid sequence selected from the group consisting of: SEQ ID NOS: 2, 4, 6, 8, 10, 12, 14, and 16 to a solid surface. This polypeptide is then exposed to test compounds or library of compounds and the ability of the compounds to bind to the transporter is measured. This invention also provides a compound identified by the above method.

In yet another embodiment, the invention provides cells comprising recombinant nucleic acids encoding cell membrane transporter polypeptides with greater than 70% amino acid identity to sequences selected from the group consisting of: SEQ ID NOS: 2, 4, 6, 8, 10, 12, 14, and 16; recombinant nucleic acids with sequences selected from the group consisting of: SEQ ID NOS: 1, 3, 5, 7, 9, 11, 13, and 15; and recombinant nucleic acids encoding polypeptides with amino acid sequences selected from the group consisting of: SEQ ID NOS: 2, 4, 6, 8, 10, 12, 14, and 16.

BRIEF DESCRIPTION OF SEQUENCE IDENTIFIERS

SEQ ID NO: 1 refers to the nucleotide sequence of the *Manduca sexta* acetylcholine transporter.

SEQ ID NO: 2 refers to the amino acid sequence of the *Manduca sexta* acetylcholine transporter.

SEQ ID NO: 3 refers to the nucleotide sequence of the *Manduca sexta* serotonin transporter.

SEQ ID NO: 4 refers to the amino acid sequence of the *Manduca sexta* serotonin transporter.

SEQ ID NO: 5 refers to the nucleotide sequence of the *Manduca sexta* proline transporter.

SEQ ID NO: 6 refers to the amino acid sequence of the *Manduca sexta* proline transporter.

SEQ ID NO: 7 refers to the nucleotide sequence of the *Aedes aegypti* glutamate transporter.

SEQ ID NO: 8 refers to the amino acid sequence of the *Aedes aegypti* glutamate transporter.

SEQ ID NO: 9 refers to the nucleotide sequence of the *Manduca sexta* neurotransmitter transporter encoded by the inebriated gene.

SEQ ID NO: 15 refers to the nucleotide sequence of the *Aedes aegypti* LAT transporter.

SEQ ID NO: 16 refers to the amino acid sequence of the *Aedes aegypti* LAT transporter.

DESCRIPTION OF THE SPECIFIC EMBODIMENTS

I. Definitions

"Insect cell membrane transporter" refers to a gene, or the protein it encodes, that in its wildtype form has the ability to transport a compound across an insect cell membrane. If an insect cell membrane transporter gene is damaged (e.g., by radiation, a carcinogen or inherited, or spontaneous mutation) or blocked from functioning (e.g., by specifically binding to another substance other than the one normally transported), it may lose its wildtype ability to transport compounds across the cell membrane. Preferred transporters include but are not limited to transporters that are present in the nervous system, alimentary canal or malpighian tubules of insects, for example, a proline transporter, an acetylcholine transporter, a serotonin transporter, a glutamate transporter, acetylcholine transporter, a neurotransmitter transporter encoded by the inebriated gene, a GABA transporter, and a LAT transporter.

The term "insect cell membrane transporter" also refers to polymorphic variants, alleles, interspecies homologs, and mutants that: (1) have about 70% amino acid sequence identity, preferably about 80–90% amino acid sequence identity to SEQ ID NOS: 2, 4, 6, 8, 10, 12, 14, or 16 over a window of about at least 50–100 amino acids; (2) binds to polyclonal antibodies raised against an immunogen comprising an amino acid sequence selected from the group consisting of SEQ ID NOS: 2, 4, 6, 8, 10, 12, 14, and 16 and conservatively modified variants thereof; (3) specifically hybridize (with a size of at least about 500, preferably at least about 900 nucleotides) under stringent hybridization conditions to a sequence selected from the group consisting of SEQ ID NOS: 1, 3, 5, 7, 9, 11, 13, and 15 and conservatively modified variants thereof; or (4) are amplified by primers that specifically hybridize under stringent conditions to the same sequence as degenerate primers, including, but not limited to, the following:

```
1S forward primer for NTTs: (A69) (SEQ ID NO:17)
5'-CGGAATTCTGG(G/C)CAA(T/C)(G/A)TITGG(A/C)GITT(C/T)CCNTA-3'

4A reverse primer for NTTs: (A67) (SEQ ID NO:18)
5'-GCCAAGCTTGAAGAAGAT(C/T)TG(G/A)GIIGCIGC(G/A)TCNA(C/T/G)CCA-3'

2S reverse primer for NTTs: (A70) (SEQ ID NO:19)
C-TCC-ATG-GA(AG)-AA(TC)-GGI-GGI-GGI-GCN-TT 3A reverse primer for NTTs: (A68) (SEQ ID NO:20)
GGC-GAG-CTC-GGC-ICC-IGG-IAG-IGT-N(AG)C-NCC
```

SEQ ID NO: 10 refers to the amino acid sequence of the *Manduca sexta* neurotransmitter transporter encoded by the inebriated gene.

SEQ ID NO: 11 refers to the nucleotide sequence of the *Manduca sexta* orphan transporter.

SEQ ID NO:12 refers to the amino acid sequence of the *Manduca sexta* orphan transporter.

SEQ ID NO: 13 refers to the nucleotide sequence of the *Manduca sexta* GABA transporter.

SEQ ID NO: 14 refers to the amino acid sequence of the *Manduca sexta* GABA transporter.

"Insecticide" refers to an agent, formulation, or preparation that destroys or controls insects, or is hostile or repellant to insects.

The terms "isolated," "purified," or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated insect cell membrane transporter nucleic acid is separated from open reading frames that flank the insect cell membrane transporter gene and encode proteins other than insect cell membrane transporters. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The terms "polypeptide," "peptide," and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group (e.g., homoserine, norleucine, methionine sulfoxide, methionine methyl sulfonium). Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alter, add or delete a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W). (see, e.g. Creighton, *Proteins* (1984)).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic*

*Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with a wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers or a pool of degenerate primers that encode a conserved amino acid sequence, can then be used as a probe under stringent hybridization conditions to isolate the test sequence from a cDNA or genomic library, or to identify the test sequence in, e.g., a Northern or Southern blot. Alternatively, another indication that the sequences are substantially identical is if the same set of PCR primers can be used to amplify both sequences.

The terms "identical" or percent "identity, "or "sequence identity" in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403–410 and Altschuel et al. (1977) *Nucleic Acids Res.* 25: 3389–3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787

(1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially an Fab with part of the hinge region (see *Fundamental Immunology* (Paul ed., 3$^{rd}$ ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies or those synthesized de novo using recombinant DNA methodologies (e.g., single chain Fv).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

The phrase "selectively associates with" refers to the ability of a nucleic acid to "selectively hybridize" with another as defined above, or the ability of a test compound to "selectively (or specifically) bind to an insect cell membrane transporter, as defined above.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Test compound" refers to any chemical compound, synthetic or naturally occurring, for example small organic molecules, peptides, or antisense nucleic acids. In the present context, such compounds are screened for ability to bind to or modulate the activity of an insect cell membrane transporter. Such compounds can be used to formulate insecticides for the destruction or control of insect populations.

"Modulates activity" refers to the ability of a compound to inhibit, activate, modulate or bind to an insect cell transporter. Such activity can be tested and measured by methods known to one of skill in the art.

The phrase "functional effects" in the context of assays for testing compounds that modulate activity of an insect cell membrane transporter includes the determination of any parameter that is indirectly or directly under the influence of the insect cell membrane transporter protein. Functional effects include, e.g., increase in flux across the membrane, decrease in flux across the membrane.

By "determining the functional effect" is meant assays for a compound that increases or decreases a parameter that is directly or indirectly under the influence of an insect cell membrane transporter. Such functional effects can be measured by any means known to those skilled in the art.

"Inhibitors," "activators," and "modulators" of insect cell membrane transporter activity refer to inhibitory, activating, or modulatory molecules identified using in vitro and in vivo assays for membrane transport, e.g., ligands, agonists, antagonists, and their homologs and mimetics. Inhibitors are compounds that decrease, block, prevent, delay activation, or inactivate membrane transport, e.g., antagonists. Activators are compounds that increase, activate, facilitate, or enhance activation of transporters, e.g., agonists. Modulators are inhibitors and activators and include genetically modified versions of insect cell membrane transporters, e.g., with altered activity, as well as naturally occurring and synthetic ligands, antagonists, agonists, small chemical molecules and the like. Such assays for modulators include, e.g., expressing an insect cell membrane transporter in cells, applying putative modulator compounds, and then determining the functional effects on inhibition of membrane transport. Compounds identified by these assays are used in insecticide preparations.

Samples or assays comprising an insect cell membrane transporter that has been treated with a potential modulator are compared to control samples without the inhibitor, activator, or modulator. Control samples (untreated with inhibitors) are assigned a relative transport activity value of 100%. Inhibition of transport is achieved when the insect cell membrane transporter activity value relative to the control is about 90%, preferably 50%, more preferably 250%. Activation of the transporter is achieved when the insect cell membrane transporter activity value relative to the control (untreated with activators) is 110%, more preferably 150%, more preferably 200–500%, more preferably 1000–3000% higher.

II. Isolation of Genes Encoding Insect Transporters

The present invention discloses the existence of novel insect transporters that can be used as targets for screening of new insecticides. The nucleic acids encoding the transporter targets disclosed here were isolated from *Manduca Sexta* $5^{th}$ instar larvae CNS, *Manduca Sexta* embryo, and *Aedes aegypti* midgut and malpighian tubules. Elucidation of the nucleic acid and amino acid sequences of these proteins and the existence of tissues/glands homologous to those used herein in many other insects and animals, provide a number of different natural sources from which these targets may be derived. Insect cell transporters are present in many insect tissues. One embodiment focuses on the transporters present in the nervous system, alimentary canal and in malpighian tubules. For example, conserved transporter sequences for use as primers are optionally identified from mammals and *C. elegans*.

A. General Recombinant DNA Methods

Insect transporter polypeptides and nucleic acids are used in the assays described below. For example, the nucleic acids and proteins can be used to identify novel insecticides and to provide target sites for insecticide action. Such polypeptides and nucleic acids can be made using routine techniques in the field of recombinant genetics. Basic texts disclosing the general methods of use in this invention include Sambrook et al., *Molecular Cloning, A Laboratory Manual* ($2^{nd}$ ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides can be chemically synthesized according to the solid phase phosphoramidite triester method first described by Beaucage & Caruthers, *Tetrahedron Letts.* 22:1859–1862 (1981), using an automated synthesizer, as described in Van Devanter et al, *Nucleic Acids Res.* 12:6159–6168 (1984). Purification of oligonucleotides is typically by either native acrylamide gel electrophoresis or by anion-exchange HPLC as described in Pearson & Reanier, *J. Chrom.* 255:137–149 (1983). The sequence of the cloned genes and synthetic oligonucleotides can be verified after cloning using, e.g., the chain termination method for sequencing double-stranded templates of Wallace et al., *Gene* 16:21–26 (1981). Again, as noted above, companies such as Operon Technologies, Inc. provide an inexpensive commercial source for essentially any oligonucleotide.

B. Cloning Methods for the Isolation of Nucleotide Sequences Encoding Insect Membrane Transporters In general, the nucleic acid sequences encoding genes of interest, such as sequences for the GABA, proline, serotonin, acetylcholine, glutamate transporters and the neurotransmitter transporter encoded by the inebriated gene, GABA transporters, and LAT transporters, as well as related nucleic acid sequence homologs, are cloned from cDNA and genomic DNA libraries by hybridization with a probe, or isolated using amplification techniques with oligonucleotide primers. Preferably insect sequences are used. For example, acetylcholine transporter sequences are typically isolated from insect nucleic acid (genomic or cDNA) libraries by hybridizing with a nucleic acid probe, the sequence of which can be derived from SEQ ID NO: 1. A suitable tissue from which insect membrane transporter RNA and cDNA can be isolated is, e.g., *Manduca sexta* embryo tissue, such as brain or ventral nerve cord tissue.

Amplification techniques using primers can also be used to amplify and isolate, e.g., a nucleic acid encoding the GABA or serotonin transporter, from DNA or RNA (see, e.g., Dieffenfach & Dveksler, *PCR Primer: A Laboratory Manual* (1995)). These primers can be used, e.g., to amplify either the full length sequence or a probe of one to several hundred nucleotides, which is then used to screen a mammalian library for the full-length nucleic acid of choice. For example, degenerate primer sets, can be used to isolate insect cell membrane transporter nucleic acids. Nucleic acids can also be isolated from expression libraries using antibodies as probes. Such polyclonal or monoclonal antibodies can be raised, e.g., using the sequence of an insect cell membrane transporter, such as the GABA transporter or proline transporter.

Polymorphic variants and alleles that are substantially identical to the gene of choice can be isolated using nucleic acid probes, and oligonucleotides under stringent hybridization conditions, by screening libraries. Alternatively, expression libraries can be used to clone, e.g., acetylcholine transporters and proline transporters, polymorphic variants, interspecies homologs, and alleles, by detecting expressed homologs immunologically with antisera or purified antibodies made against a specific transporter of interest, such as the serotonin transporter, which also recognizes and selectively binds to a serotonin transporter homolog.

To make a cDNA library, one should choose a source that is rich in the mRNA of choice, e.g., for the transporters of the invention embryo tissue from *M. sexta* is optionally used. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al, supra).

For a genomic library, the DNA is extracted from the tissue and either mechanically sheared or enzymatically digested to yield fragments of about 12–20 kb. The fragments are then separated by gradient centrifugation from undesired sizes and are constructed in non-lambda expression vectors. These vectors are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating a nucleic acid and its homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of, e.g., serotonin and proline transporters, directly from mRNA, from cDNA, from genomic libraries, or cDNA libraries. Degenerate oligonucleotides can be designed to amplify transporter homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of transporters encoding mRNA in physiological samples, for nucleic acid sequencing, or for other purposes. Genes amplified by the PCR reaction can be purified from agarose gels and cloned into an appropriate vector.

As described above, gene expression of membrane transporters can also be analyzed by techniques known in the art, e.g., reverse transcription and PCR amplification of mRNA, isolation of total RNA or poly A+RNA, northern blotting, dot blotting, in situ hybridization, RNase protection, probing high density oligonucleotides, and the like. All of these techniques are standard in the art.

Synthetic oligonucleotides can be used to construct recombinant genes for use as probes or for expression of protein. This method is performed using a series of overlapping oligonucleotides usually 40–120 bp in length, representing both the sense and non-sense strands of the gene. These DNA fragments are then annealed, ligated and cloned. Alternatively, amplification techniques can be used with precise primers to amplify a specific subsequence of a transporter nucleic acid. The specific subsequence is then ligated into an expression vector.

The nucleic acid encoding the protein of choice is typically cloned into intermediate vectors before transformation into prokaryotic or eukaryotic cells for replication and/or expression. These intermediate vectors are typically prokaryote vectors, e.g., plasmids, or shuttle vectors. Optionally, cells can be transfected with recombinant transporter nucleic acids operably linked to a constitutive promoter, to provide higher levels of transporter expression in cultured cells.

C. Expression in Prokaryotes and Eukaryotes

To obtain high level expression of a cloned gene or nucleic acid, such as those cDNAs encoding the cell membrane transporters of the invention, one typically subclones the transporter of interest, e.g., the acetylcholine or serotonin transporter, into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the transporter proteins are available in, e.g., *E. coli*, Bacillus sp., and Salmonella (Palva et al., *Gene* 22:229–235 (1983)). Kits for such expression systems are commercially available. Eukaryotic expression systems for mammalian cells, yeast, and insect cells are well known in the art and are also commercially available. For example, the GABA transporter is optionally expressed in *Xenopus oocytes*.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function. The promoter typically also includes elements that are responsive to transactivation, e.g., hypoxia responsive elements, Gal4 responsive elements, lac repressor responsive elements, and the like. The promoter can be constitutive or inducible, heterologous or homologous.

In addition to the promoter, the expression vector typically contains a transcription unit or expression cassette that contains all the additional elements required for the expression of the nucleic acid in host cells. A typical expression cassette thus contains a promoter operably linked, e.g., to the nucleic acid sequence encoding the transporter of interest, and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a transporter encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619–17622 (1989); *Guide to Protein Purification, in*

*Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

After the expression vector is introduced into the cells, the transfected cells are cultured under conditions favoring expression of the cell membrane transporter protein, which is recovered from the culture using standard techniques identified below.

III. Purification of Insect Cell Membrane Transporter Peptides

If necessary, naturally occurring or recombinant proteins can be purified for use in functional assays, e.g., to make antibodies to detect transporters, or to use in screening applications as discussed below. Naturally occurring cell membrane transporters, e.g., proline, serotonin, glutamate, or acetylcholine transporters, are purified, e.g., from tissue such as the brain, central nervous system, gut, embryo or even whole insects or any other source of a transporter homolog. Recombinant transporters are purified from any suitable expression system, e.g., by expressing a serotonin transporter in *E. coli* and then purifying the recombinant protein via affinity purification, e.g., by using antibodies that recognize a specific epitope on the protein or on part of the fusion protein, or by using glutathione affinity gel, which binds to GST. In some embodiments, the recombinant protein is a fusion protein, e.g., with GST or Gal4 at the N-terminus.

The protein of choice may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant protein is being purified. For example, proteins having established molecular adhesion properties can be reversibly fused to a cell membrane transporter protein, such as proline or acetylcholine transporters. With the appropriate ligand, the cell membrane transporter of interest can be selectively adsorbed to a purification column and then freed from the column in a relatively pure form. The fused protein is then removed by enzymatic activity. Finally, the transporters of interest could be purified using immunoaffinity columns.

A. Purification of Cell Membrane Transporters from Recombinant Bacteria

Recombinant proteins are expressed by transformed bacteria in large amounts, typically after promoter induction. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of activity. Although guanidine hydrochloride and similar agents are denaturants, this denaturation is not irreversible and renaturation may occur upon removal (by dialysis, for example) or dilution of the denaturant, allowing re-formation of biologically active protein. Other suitable buffers are known to those skilled in the art. The protein of choice is separated from other bacterial proteins by standard separation techniques, e.g., with Ni—NTA agarose resin.

Alternatively, it is possible to purify the recombinant transporter protein from bacteria periplasm. After lysis of the bacteria, when the protein is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Cell Membrane Transporters Solubility Fractionation Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the cell membrane transport protein, e.g. GABA, proline, or serotonin transporters, can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The cell membrane transporter protein of choice can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

IV. Immunological Detection of Cell Membrane Transporters

In addition to the detection of cell membrane transporter genes and gene expression using nucleic acid hybridization technology, one can also use immunoassays to detect the cell membrane transporters of the invention, e.g., to identify alleles, mutants, polymorphic variants and interspecies homologs of insect cell membrane transporters. Immunoassays can be used to qualitatively or quantitatively analyze transporters, e.g., to detect the presence of a transporter protein, to measure transporter activity, or to identify modulators of transporter activity. A general overview of the applicable technology can be found in Harlow and Lane, *Antibodies: A Laboratory Manual* (1988).

A. Antibodies to Insect Cell Membrane Transporters

Methods of producing polyclonal and monoclonal antibodies that react specifically with the cell membrane transporters of the invention, e.g., SEQ ID NOS: 2, 4, 6, 8, 10, 12, 14, and 16 are known to those of skill in the art (see, e.g. Coligan, *Current Protocols in Immunology* (1991); Harlow & Lane, supra; Goding, *Monoclonal Antibodies: Principles and Practice* (2$^{nd}$ ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)). In addition, as noted above, many companies, such as BMA Biomedicals, Ltd., HTI Bio-products, and the like, provide the commercial service of making an antibody to essentially any peptide.

A number of cell membrane transporter comprising immunogens may be used to produce antibodies specifically reactive with particular insect cell membrane transporters. For example, recombinant proline or serotonin transporters, or antigenic fragments thereof, are isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used as an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. To improve reproducibility, an inbred strain of mice (e.g., BALB/C mice) can be immunized to make the antibody; however, standard animals (mice, rabbits, etc.) used to make antibodies are immunized with the protein using a standard adjuvant, such as Freund's adjuvant, and a standard immunization protocol (see Harlow & Lane, supra). The animal's immune response to the immunogen preparation is monitored by taking test bleeds and determining the titer of reactivity to the protein of choice. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen.

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-cell membrane transporter proteins or even other related proteins, e.g., from other organisms, using a competitive binding immunoassay. Specific polyclonal antisera and monoclonal antibodies will usually bind with a $K_D$ of at least about 0.1 mM, more usually at least about 1 $\mu$M, preferably at least about 0.1 $\mu$M or better, and most preferably, 0.01 $\mu$M or better.

Once cell membrane transporter specific antibodies are available, these proteins can be detected by a variety of immunoassay methods. For a review of immunological and immunoassay procedures, see *Basic and Clinical Immunology* (Stites & Terr eds., 7$^{th}$ ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

Cell membrane transporters, such as GABA or acetylcholine transporters, can be detected and/or quantified using any of a number of well recognized immunological binding assays (see, e.g., U.S. Pat. Nos. 4,366,241; 4,376,110; 4,517, 288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case a cell membrane transporter, or antigenic fragments thereof). The antibody may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled cell membrane transporter polypeptide or a labeled anti-membrane transporter antibody. The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

V. Screening Assays for Compounds that Modulate Transporter Activity

Insect cell membrane transporters and their alleles, interspecies homologs, and polymorphic variants participate in transport of a wide variety of molecules across cell membranes. For example, GABA, which is present in various regions of central nervous systems, has been shown to inhibit neuronal activity in *M. sexta* antennal lobes, suggesting its involvement in regulating central nervous function in this insect. Therefore, compounds that activate or inhibit the GABA transporter action would affect regulation of the central nervous system. Similarly, inhibition of the serotonin transporter would affect nervous system function and consequently insect activity. Any of these changes in transport across cell membranes can be assessed by using a variety of in vitro and in vivo assays, e.g., stable or transient cell lines expressing the transporter, labeled neurotransmitters, or electrophysiology.

Furthermore, these assays can be used to screen for activators, inhibitors, and modulators of transporter activity. Such activators, inhibitors, and modulators of transporter activity can then be used in insecticides. For example, compounds such as Nipecotic acid, L-DABA, β-alanine, BABA, ACHC, and hemicholinium, guvacine hydrochloride, and cocaine hydrochloride can be prepared in a buffer, such as (Buffer B), and introduced into the transport chamber as part of an assay for detecting transporter inhibition or activation. Compounds that are of interest include analogs of neurotransmitters, natural products, venoms and those from combinatorial libraries. Compounds found to inhibit a transport function necessary, e.g., for central nervous system function, are then optionally used in insecticide formulations.

Biologically active or inactivated transporter polypeptides, either recombinants or naturally occurring, are used to screen for activators, inhibitors, or modulators of transport mechanisms. The transporter polypeptides can be recombinantly expressed in a cell, naturally expressed in a cell, recombinantly or naturally expressed in cells transplanted into an animal or plant, or recombinantly or naturally expressed in a transgenic animal. Modulation is tested using one of the in vitro or in vivo assays described herein.

Cells that have wildtype transporter genes, transporter null mutations, transporter missense mutations, or inactivation of membrane transporters are used in the assays of the invention, both in vitro and in vivo. Preferably, insect cells are used. Optionally, the cells can be transfected with an exogenous transporter gene operably linked to a constitutive promoter, to provide higher levels of transporter expression. Alternatively, endogenous transporter levels can be examined. The cells can be treated to induce transporter expression. The cells can be immobilized, be in solution, be injected into an animal, or be naturally occurring in a transgenic or non-transgenic animal or plant.

Samples or assays that are treated with a test compound which potentially activates, inhibits, or modulates membrane transporters are compared to control samples that are not treated with the test compound, to examine the extent of modulation. Generally, the compounds to be tested are present in the range from 1 nM to 1000 µM. Control samples (untreated with activators, inhibitors, or modulators) are assigned a relative transporter activity value of 100%. Inhibition of transporter activity is achieved when the transporter activity value relative to the control is about 90% (e.g., 10% less than the control), preferably 50%, more preferably 25%. Activation of transporters is achieved when the transporter activity value relative to the control is 110% (e.g., 10% more than the control), more preferably 150%, more preferably 200% higher.

The effects of the test compounds upon the function of the transporter polypeptides can be measured by examining any one of a variety of parameters. For example, parameters such as the affinity, specificity, and inhibition of transport, can be measured. Furthermore, the effects of the test compounds on the transporter protein or mRNA levels, transcriptional activation or repression of a reporter gene can be measured. In each assay, cells expressing membrane transporters are contacted with a test compound and incubated for a suitable amount of time, typically 1–30 minutes. Then, parameters such as those described above are compared to those produced by control cells untreated with the test compound.

In one embodiment, the effect of test compounds upon the function of transporter can be determined by comparing the level of transporter protein or mRNA in treated samples and control samples. The level of transporter protein is measured using immunoassays such as western blotting, ELISA and the like with a transporter specific antibody. For measurement of mRNA, amplification, e.g., using PCR, LCR, or hybridization assays, e.g., northern hybridization, RNase protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using the transporter promoter operably linked to a reporter gene such as luciferase, green fluorescent protein, CAT, or β-gal. After treatment with a potential transporter modulator, the amount of reporter gene transcription, translation, or activity is measured according to standard techniques known to those of skill in the art.

The compounds tested as modulators of transporter activity can be any chemical compound, or biological entity, such as a protein, sugar, nucleic acid or lipid. Alternatively, modulators can be genetically altered versions of the transporter of interest. For example, an antisense construct of a transporter can be used as a modulator.

Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland), and combinatorial libraries produced by chemical companies.

In one preferred embodiment, high throughput screening methods involve providing a combinatorial chemical or peptide library containing a large number of potential therapeutic compounds (potential modulator or inhibitor compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual insecticides.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al.,*J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing a membrane transporter of the invention is attached to a solid phase substrate. In the high throughput assays of the invention, it is possible to screen up to several thousand different modulators or inhibitors in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100–about 1500 different compounds. It is possible to assay several different plates per day; assay screens for up to about 6,000–20,000 different compounds is possible using the integrated systems of the invention. More recently, microfluidic approaches to reagent manipulation have been developed, e.g., by Caliper Technologies (Palo Alto, Calif.).

Yet another assay for compounds that modulate transporter activity involves computer assisted drug design, in which a computer system is used to generate a three-dimensional structure of a transporter based on the structural information encoded by the amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering the transporter amino acid sequences of at least 10 amino acid residues or corresponding nucleic acid sequences encoding a transporter polypeptide into the computer system. The amino acid sequence of the polypeptide or the nucleic acid encoding the polypeptide is selected from the group consisting of SEQ ID NOS: 2, 4, 6, 8, 10, 12, 14, and 16 and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art. The three-dimensional structural model of the protein can be saved to a computer readable form and be used for further analysis (e.g., identifying potential ligand binding regions of the protein and screening for mutations, alleles and interspecies homologs of the gene).

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the transporter protein to identify ligands that bind to transporter. Binding affinity between the protein and ligands is determined using energy terms to determine which ligands have an enhanced probability of binding to the protein. The results, such as three-dimensional structures for potential ligands and binding affinity of ligands, can also be saved to a computer readable form and can be used for further analysis (e.g., generating a three dimensional model of mutated proteins having an altered binding affinity for a ligand).

VI. Insecticidal Preparations

The present invention will be particularly useful in the formulation and development of preparations for use in the control of insects. In particular embodiments of insecticide preparations, a composition comprises, as an active ingredient, a test compound, identified in the screening assays described above, that inhibits, activates, or modulates activity of an insect cell membrane transporter, e.g., a proline transporter, a serotonin transporter, an acetylcholine transporter. Combinations of test compounds that modulate a variety of transporters may also be used in insecticide preparations.

Bioactive peptides and peptide fragments identified by the assays above as modulating insect cell membrane transporter activity may be formulated in DMSO, or other suitable carrier, to enhance the permeability of the preparation through insect cuticle. This preparation may then be applied as a spray or delivered into a water source as an insect control strategy.

Organic molecules identified through the screening assays described above may also be formatted for use as an insect spray, water treatment, or bait.

In one particular application, a sense, an antisense, or combination of sense and antisense sequences for one or a combination of the insect cell membrane transporters will be engineered into a virus using standard techniques.

For use as an insecticide, the virus carrying the membrane transport antisense sequence(s) will be formulated according to standard field application protocols, and then sprayed, by way of example, onto crops. The occluded virus (OV) is an example of a suitable virus carrier to be used in these applications, these viruses entering the insect via an oral route and solubilized in the alkaline midgut, thus releasing the embedded virions. The virions will enter the midgut cells and subsequently enter the hemocoel as budded virus (BV), and will then be transported to other tissues via the circulatory system and along the tracheal network via epidermal cells. The infection process will result in cessation of insect feeding within 5–7 days.

Application of antisense engineered sequences may be used to provide effective delivery of anti-hormone sequences to pest populations, and be expected to prevent successful insect molting.

In a particular embodiment, viral constructs comprising sense sequences for insect cell membrane transporters are provided, and comprise a sequence essentially as set forth in SEQ ID NOS: 1, 3, 5, 7, 9, 11, 13, and 15, which includes the sequences for the proline transporter, acetylcholine transporter, serotonin transporter, glutamate transporter, neurotransmitter transporter encoded by the inebriated gene, and an orphan transporter, a GABA transporter, and a LAT transporter. Viral vectors with each of the sequences are optionally constructed using a baculovirus vector pACUW21. However, other vectors may be used together with these and other of the insect cell membrane transporter encoding sequences, and used in insecticidal preparations.

By way of example, a viral delivery system such as pAcUW2B under the control of a p10 promoter (Stewart et al., 1991) may also be used. Other viral systems, such as those described by Tomalski et al. (1991), and Maeda et al., (1991) also are considered useful in the practice of the present invention, these teachings also being specifically incorporated herein by reference.

The insect cell membrane transporter encoding nucleic acid molecules of the present invention may also be used to transform plants. For example, these coding nucleic acid sequences are optionally used either alone or in combination to transform vegetable and fruit plants. Such may be used as part of a method to enhance insect susceptibility to ecdysis triggering hormone like activity, particularly where it is co-expressed with a suitable gut-permeating agent, such as Bacillus thuringensis or viral proteins.

The test compounds of the invention that modulate the activity of insect cell membrane transporters are optionally formulated in microbial delivery systems for application to plants, animals, or both, as a spray or bait. Examples of these preparations are described below. The various topically active preparations that bind insect cell membrane transporters may be formulated directly into a spray or bait for use in the control of insects by applying to plants and animals.

The modulators, inhibitors, and activators of insect cell membrane transport, and their related homologs for agricultural use will be formulated in a manner appropriate for field application, as sprays, or baits, for release into aquatic environments, and for use in urban dwellings. Treatments for cockroaches, ticks, fleas, termites and other common pests may thus be conveniently and relatively easily provided using the preparations of the present disclosure.

Topically active preparations of the present invention, such as compounds that bind the insect cell membrane transporter, may be formulated for application to agricultural crops and other plants to control insect populations, for example lepidopteran insect populations. Economic loss to a variety of important agricultural crops, including vegetable crops, cotton, grains, such as corn, wheat and soybeans, attributable to lepidopteran insects, may thus be reduced. Insecticides that include the compounds characterized using the present invention provide alternative approaches for controlling against loss attributable to many varieties of insects without toxicity to other animals and humans.

Modulators of insect cell membrane transporter are effective for inducing developmental effects when injected into the insect. For topically active formulations, a gene encoding the modulator or homolog or biologically active fragment thereof, will be included with a virus and the virus applied to crops (or animals) that are at risk of harboring the insects pests, such as lepidopteran. Alternatively, the effectiveness of these preparations may be further enhanced by including within the virus a neurotoxin that will act to paralyze the virus. Additionally, insect cell membrane transporter binding molecules may be prepared as a topically active insecticide.

EXAMPLES

The following examples are provided by way of illustration only and not by way of limitation. Those of skill in the art will readily recognize a variety of noncritical parameters that could be changed or modified to yield essentially similar or desirably different results.

This example describes a protocol for screening compounds for inhibition of insect cell membrane transporters.

Stably or transiently transformed cell lines expressing the transporter in a 24-, 96-, 384- or 1536-well format are exposed for 5–30 minutes to a compound either singly or in a combinatorial form. The exposed cells are analyzed using standard assays for measuring transport capacity. A decrease in transport activity indicates the potential of a compound to inhibit transport.

To screen for compounds affecting the serotonin transporter, CV-1 cells transiently expressing the Manduca sexta transporter are plated at ca. $5 \times 10^5$ in a 24-well tissue culture plate in tissue culture media. The cells are either preincubated with an inhibitor or the inhibitor is added simultaneously with the serotonin. A range of inhibitor concentrations is used. To monitor transport, $^3$H-labeled serotonin is added and the cells are incubated for 15 minutes. The cells are then washed twice with buffer and the uptake of serotonin assessed by scintillation counting.

What is claimed is:

1. An isolated nucleic acid encoding an insect cell serotonin transporter polypeptide, wherein the nucleic acid encodes a polypeptide comprising SEQ ID NO: 4.

2. An isolated nucleic acid encoding an insect cell serotonin transporter polypeptide, wherein the nucleic acid comprises SEQ ID NO: 3.

3. An isolated insect cell serotonin transporter polypeptide wherein the polypeptide comprises SEQ ID NO: 4.

4. A cell comprising a recombinant nucleic acid encoding an insect cell membrane serotonin transporter polypeptide, comprising SEQ ID NO: 4.

5. The cell of claim 4, wherein the cell is a mammalian CV-1 cell.

6. A method of screening for a compound which modulates activity of an insect cell membrane transporter, the method comprising the steps of:
   a) contacting a recombinant cell with a test compound, wherein the recombinant cell comprises a recombinant nucleic acid expressing the insect cell membrane transporter, and
   b) determining the ability of the test compound to modulate activity of the insect cell membrane transporter, and
   wherein said nucleic acid encoding the cell membrane transporter is selected from the group consisting of: SEQ ID NO: 3 and nucleic acids encoding the amino acid sequence of SEQ ID NO: 4.

7. The method of claim 6, wherein the cell is selected from the group consisting of: an insect cell, a mammalian cell, and a yeast cell.

8. A method of screening for a compound which binds to an insect cell membrane transporter, the method comprising the steps of:
   a) attaching an insect cell membrane transporter polypeptide to a solid surface; wherein the cell membrane transporter polypeptide is SEQ ID NO: 4; and
   b) exposing the polypeptide to a test compound or a library of test compounds; and
   c) determining the ability of the test compound or library of test compounds to bind to the cell membrane transporter.

* * * * *